(12) United States Patent
Graessle et al.

(10) Patent No.: US 8,094,916 B2
(45) Date of Patent: Jan. 10, 2012

(54) BIOLOGICAL GROWTH PLATE SCANNER

(75) Inventors: Josef A. Graessle, Meerbuscher (DE); Stephen B. Schenk, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/004,925

(22) Filed: Jan. 12, 2011

(65) Prior Publication Data
US 2011/0102582 A1 May 5, 2011

Related U.S. Application Data

(63) Continuation of application No. 10/305,722, filed on Nov. 27, 2002, now abandoned.

(51) Int. Cl.
G06K 9/00 (2006.01)
(52) U.S. Cl. ........................................ 382/133
(58) Field of Classification Search .................. None
See application file for complete search history.

(56) References Cited

U.S. PATENT DOCUMENTS

| | | | |
|---|---|---|---|
| 3,493,772 A | 2/1970 | Daughters et al. | |
| 3,745,090 A | 7/1973 | Chappelle et al. | 195/103 |
| 3,811,036 A | 5/1974 | Perry | |
| 3,962,040 A | 6/1976 | Campbell et al. | 195/127 |
| 4,118,280 A | 10/1978 | Charles et al. | |
| 4,146,775 A | 3/1979 | Kirchner et al. | 219/295 |
| 4,160,601 A | 7/1979 | Jacobs et al. | 356/404 |
| 4,353,988 A | 10/1982 | Couse et al. | |
| 4,563,096 A | 1/1986 | Chidlow et al. | 356/440 |
| 4,591,567 A | 5/1986 | Britten et al. | |
| 4,637,053 A | 1/1987 | Schalkowsky | |
| 4,720,463 A | 1/1988 | Farber et al. | |
| 4,724,215 A | 2/1988 | Farber et al. | |
| 4,817,785 A | 4/1989 | Farber et al. | |
| 4,856,073 A | 8/1989 | Farber et al. | |
| 5,099,521 A | 3/1992 | Kosaka | 382/6 |
| 5,117,467 A | 5/1992 | Misaki et al. | |

(Continued)

FOREIGN PATENT DOCUMENTS

DE 19819144 4/1998
(Continued)

OTHER PUBLICATIONS

Decision on Appeal dated Dec. 2, 2008 in U.S. Appl. No. 10/306,663, filed Nov. 27, 2002 (18 pgs.).

(Continued)

Primary Examiner — Yuzhen Ge

(57) ABSTRACT

A biological growth plate scanner includes a multi-color illumination system that illuminates a biological growth plate with different illumination colors. A monochromatic image capture device captures images of the biological growth plate during illumination of the growth plate with each of the illumination colors. A processor combines the images to form a composite multi-color image, and/or individual components of the composite image, and analyzes the composite image to produce an analytical result such as a colony count or a presence/absence result. The biological growth plate scanner may include both front and back illumination components. The back illumination component may include a diffuser element disposed under the biological growth plate. The diffuser element receives light from one or more laterally disposed illumination sources, and distributes the light to illuminate a back side of the biological growth plate. The illumination sources in the front and back illumination components may take the form of sets of light emitting diodes (LEDs) that can be independently controlled by the processor.

16 Claims, 14 Drawing Sheets

U.S. PATENT DOCUMENTS

| | | | |
|---|---|---|---|
| 5,202,010 A | 4/1993 | Guzman | 204/299 |
| 5,270,173 A | 12/1993 | Yonemori et al. | 435/29 |
| 5,290,701 A | 3/1994 | Wilkins | |
| 5,329,686 A | 7/1994 | Kildal et al. | |
| 5,364,766 A | 11/1994 | Mach et al. | |
| 5,366,873 A | 11/1994 | Eden et al. | |
| 5,372,485 A | 12/1994 | Sumser et al. | |
| 5,372,936 A | 12/1994 | Fraatz et al. | |
| 5,375,043 A | 12/1994 | Tokunaga | |
| 5,403,722 A | 4/1995 | Floeder et al. | |
| 5,428,690 A | 6/1995 | Bacus et al. | |
| 5,448,652 A | 9/1995 | Vaidyanathan et al. | |
| 5,491,567 A | 2/1996 | Morikawa et al. | 358/498 |
| 5,510,246 A | 4/1996 | Morgan | |
| 5,539,517 A | 7/1996 | Cabib et al. | 356/456 |
| 5,573,950 A | 11/1996 | Graessle et al. | |
| 5,591,974 A | 1/1997 | Troyer et al. | 250/336 |
| 5,671,290 A | 9/1997 | Vaidyanathan | |
| 5,694,478 A | 12/1997 | Braier et al. | |
| 5,721,435 A | 2/1998 | Troll | |
| 5,723,308 A | 3/1998 | Mach et al. | 435/34 |
| 5,744,322 A | 4/1998 | Krejcarek et al. | |
| 5,747,333 A | 5/1998 | Jungmann-Campello et al. | |
| 5,781,311 A | 7/1998 | Inoue et al. | |
| 5,787,189 A | 7/1998 | Lee et al. | |
| 5,817,475 A | 10/1998 | Gibbs et al. | 435/29 |
| 5,817,508 A | 10/1998 | Berndt | 535/287 |
| 5,956,158 A * | 9/1999 | Pinzarrone et al. | 358/474 |
| 5,995,645 A | 11/1999 | Soenksen et al. | |
| 6,002,789 A | 12/1999 | Olsztyn et al. | |
| 6,058,209 A | 5/2000 | Vaidyanathan et al. | 382/203 |
| 6,096,272 A | 8/2000 | Clark et al. | |
| 6,107,054 A | 8/2000 | Gibbs | 435/32 |
| 6,134,354 A | 10/2000 | Lee et al. | 382/270 |
| 6,238,076 B1 * | 5/2001 | Pascale et al. | 362/558 |
| 6,238,879 B1 | 5/2001 | Gibbs | |
| 6,243,486 B1 | 6/2001 | Weiss | 380/133 |
| 6,271,022 B1 | 8/2001 | Bochner | |
| 6,319,668 B1 | 11/2001 | Nova et al. | 435/6 |
| 6,372,485 B1 | 4/2002 | Clark et al. | 435/288.7 |
| 6,375,335 B1 * | 4/2002 | Tabata et al. | 362/612 |
| 6,381,353 B1 | 4/2002 | Weiss | 382/133 |
| 6,418,180 B1 | 7/2002 | Weiss | 377/6 |
| 6,459,994 B1 | 10/2002 | Parekh et al. | 702/19 |
| 6,485,979 B1 | 11/2002 | Kippenhan et al. | |
| 6,488,890 B1 | 12/2002 | Kirckof | |
| 6,583,791 B2 * | 6/2003 | Berryman et al. | 345/589 |
| 6,623,142 B1 * | 9/2003 | Lippmann et al. | 362/293 |
| 6,642,953 B1 | 11/2003 | Nieto Velasco et al. | 348/61 |
| 6,673,315 B2 | 1/2004 | Sheridan et al. | |
| 6,685,327 B2 * | 2/2004 | Dorrie | 362/27 |
| 6,690,470 B1 | 2/2004 | Baer et al. | |
| 6,711,283 B1 | 3/2004 | Soenksen | 382/133 |
| 6,716,588 B2 | 4/2004 | Sammak et al. | 435/7 |
| 6,737,266 B1 | 5/2004 | Wicks et al. | 435/288 |
| 6,999,607 B2 | 2/2006 | Kiros et al. | 382/128 |
| 7,057,721 B2 | 6/2006 | Gardiner, Jr. et al. | 356/301 |
| 7,298,885 B2 | 11/2007 | Green et al. | 382/133 |
| 7,298,886 B2 | 11/2007 | Plumb et al. | 382/133 |
| 7,319,031 B2 | 1/2008 | Vent et al. | 435/286 |
| 7,351,574 B2 | 4/2008 | Vent | 435/286 |
| 7,496,225 B2 | 2/2009 | Graessle et al. | 382/133 |
| 7,738,689 B2 | 6/2010 | Plumb et al. | 382/133 |
| 7,865,008 B2 | 1/2011 | Graessle et al. | 382/133 |
| 7,901,933 B2 | 3/2011 | Green et al. | 435/287 |
| 7,957,575 B2 | 6/2011 | Plumb et al. | 382/133 |
| 2001/0031502 A1 | 10/2001 | Watson, Jr. et al. | |
| 2001/0041347 A1 | 11/2001 | Sammak et al. | 435/7.23 |
| 2002/0025082 A1 | 2/2002 | Kaushikkar et al. | 382/294 |
| 2002/0064867 A1 | 5/2002 | Clark et al. | |
| 2002/0137091 A1 | 9/2002 | Luttermann et al. | 435/7.1 |
| 2002/0159002 A1 * | 10/2002 | Chang | 349/61 |
| 2002/0167161 A1 | 11/2002 | Butland | 283/72 |
| 2002/0191825 A1 | 12/2002 | Parekh et al. | 382/72 |
| 2003/0016406 A1 * | 1/2003 | Hoshino et al. | 358/509 |
| 2004/0032659 A1 * | 2/2004 | Drinkwater | 359/558 |
| 2004/0071342 A1 | 4/2004 | Locht et al. | 382/164 |
| 2004/0101189 A1 | 5/2004 | Green et al. | |
| 2004/0101951 A1 | 5/2004 | Vent et al. | |
| 2004/0101952 A1 | 5/2004 | Vent | |
| 2004/0101954 A1 | 5/2004 | Graessle et al. | |
| 2004/0102903 A1 | 5/2004 | Graessle et al. | |
| 2005/0053265 A1 | 3/2005 | Graessle et al. | 382/128 |
| 2005/0053266 A1 | 3/2005 | Plumb et al. | 382/128 |
| 2005/0095665 A1 | 5/2005 | Williams et al. | 435/34 |
| 2005/0222778 A1 | 10/2005 | Levinson et al. | 702/19 |
| 2006/0263258 A1 | 11/2006 | Harris et al. | 422/99 |
| 2008/0003562 A1 | 1/2008 | Plumb et al. | 435/3 |
| 2010/0232660 A1 | 9/2010 | Graessle et al. | 382/128 |
| 2010/0266192 A1 | 10/2010 | Plumb et al. | 382/133 |
| 2010/0330610 A1 | 12/2010 | Green et al. | 435/29 |

FOREIGN PATENT DOCUMENTS

| | | |
|---|---|---|
| EP | 0 008 826 A2 | 3/1980 |
| EP | 0 088 601 A1 | 9/1983 |
| EP | 0 301 600 | 1/1989 |
| EP | 0 397 256 A2 | 11/1990 |
| EP | 0 397 256 A3 | 11/1990 |
| EP | 0 429 030 A2 | 5/1991 |
| EP | 0 429 030 A3 | 5/1991 |
| EP | 0 193 385 B1 | 7/1992 |
| EP | 0 547 709 A2 | 6/1993 |
| EP | 0 547 709 A3 | 6/1993 |
| EP | 0 819 930 A2 | 1/1998 |
| EP | 1 074 610 | 2/2001 |
| EP | 0 895 086 | 11/2004 |
| GB | 2 249 829 A | 5/1992 |
| JP | 60-83597 | 5/1985 |
| JP | 5-249105 | 9/1993 |
| JP | 6-98220 | 4/1994 |
| JP | 6-109545 | 4/1994 |
| JP | 7-275200 | 10/1995 |
| JP | 10-24283 | 1/1998 |
| JP | 10-500302 | 1/1998 |
| JP | 11-500648 | 1/1999 |
| JP | 2000-270840 | 10/2000 |
| JP | 2001-242082 | 7/2001 |
| JP | 2002-538440 | 11/2002 |
| WO | WO 91/06911 | 5/1991 |
| WO | WO 92/12233 | 7/1992 |
| WO | WO 94/01528 | 1/1994 |
| WO | WO 94/26926 | 11/1994 |
| WO | WO 95/16768 | 6/1995 |
| WO | WO 95/31732 | 11/1995 |
| WO | WO 96/18721 | 6/1996 |
| WO | WO 97/15229 | 1/1997 |
| WO | WO 98/53301 | 11/1998 |
| WO | WO 98/59314 | 12/1998 |
| WO | WO 99/28436 | 6/1999 |
| WO | WO 00/32807 | 6/2000 |
| WO | WO 00/49129 | 8/2000 |
| WO | WO 00/49130 | 8/2000 |
| WO | WO 00/51058 | 8/2000 |
| WO | WO 00/65094 | 11/2000 |
| WO | WO 01/04828 | 1/2001 |
| WO | WO 01/09371 | 2/2001 |
| WO | WO 01/83673 A2 | 11/2001 |
| WO | WO 02/90966 | 1/2002 |
| WO | WO 02/37938 | 5/2002 |
| WO | WO 02/38724 | 5/2002 |
| WO | WO 02/46354 | 6/2002 |
| WO | WO 02/066961 | 8/2002 |
| WO | WO 03/014400 | 2/2003 |
| WO | WO 03/038413 | 5/2003 |

OTHER PUBLICATIONS

Kalasnsky, Kathryn S. et al.; "Raman Chemical Imaging Spectroscopy Reagentless Detection and Identification of Pathogens: Signature Development and Evaluation"; Analytical Chemistry; 2007; 79 (7) pp. 2658-2673.

Gilchrist et al., "Spiral Plate Method for Bacterial Determination", Applied Microbiology, Feb. 1973, vol. 25, No. 2, pp. 244-252.

Ilya et al.; "Streamlines Yeast Colorimetric Reporter Activity Assays Using Scanners and Plate Readers", BioTechniques, vol. 29, No. 2, Aug. 2000.

K. M. Wright et al., "Determination of Mean Growth Parameters of Bacterial Colonies Immobilized in Gelatin Gel Using a Laser Gel-Cassette Scanner", International Journal of Food Microbiology. 2000, pp. 75-89.

Corkidi et al.; "*COVASIAM: an Image Analysis Method That Allows Detection of Confluent Microbial Colonies and Colonies of Various Sizes for Automated Counting*", Applied and Environmental Microbiology, vol. 64, No. 4; Apr. 1998, pp. 1400-1404.

Product brochure entitled "Powerful data handling for GLP conformance" by ProtoCOL, Symbiosis, a division of Synoptic Ltd, Cambridge, UK (4 pgs.).

Product brochure entitled "Efficient Batch Handling" by ProtoZONE, Symbiosis, a division of Synoptic Ltd., Cambridge, UK (4 pgs.).

Product brochure entitled "Petrifilm™ Information Management System—Reduce Operational Costs and Increase Productivity"; 3M Microbiology Products; 1999; 70-2009-1996-0; (3 pgs.).

\* cited by examiner

US 8,094,916 B2

BIOLOGICAL GROWTH PLATE SCANNER

CROSS REFERENCE TO RELATED APPLICATIONS

This application is a continuation of U.S. patent application Ser. No. 10/305,722, filed Nov. 27, 2002, now abandoned which is incorporated herein by reference.

FIELD

The invention relates to scanners for analysis of biological growth media to analyze bacteria or other biological agents in food samples, laboratory samples, and the like.

BACKGROUND

Biological safety is a paramount concern in modern society. Testing for biological contamination in foods or other materials has become an important, and sometimes mandatory requirement for developers and distributors of food products. Biological testing is also used to identify bacteria or other agents in laboratory samples such as blood samples taken from medical patients, laboratory samples developed for experimental purposes, and other types of biological samples. Various techniques and devices can be utilized to improve biological testing and to streamline and standardize the biological testing process.

In particular, a wide variety of biological growth media have been developed. As one example, biological growth media in the form of growth plates have been developed by 3M Company (hereafter "3M") of St. Paul, Minn. Biological growth plates are sold by 3M under the trade name PETRIFILM plates. Biological growth plates can be utilized to facilitate the rapid growth and detection and enumeration of bacteria or other biological agents commonly associated with food contamination, including, for example, aerobic bacteria, *E. coli*, coliform, enterobacteriaceae, yeast, mold, *Staphylococcus aureus, Listeria, Campylobacter*, and the like. The use of PETRIFILM plates, or other growth media, can simplify bacterial testing of food samples.

Biological growth media can be used to identify the presence of bacteria so that corrective measures can be performed (in the case of food testing) or proper diagnosis can be made (in the case of medical use). In other applications, biological growth media may be used to rapidly grow bacteria or other biological agents in laboratory samples, e.g., for experimental purposes.

Biological growth plate scanners refer to devices used to read or count bacterial colonies, or the amount of a particular biological agent on a biological growth plate. For example, a food sample or laboratory sample can be placed on a biological growth plate, and then the plate can be inserted into an incubation chamber. After incubation, the biological growth plate can be placed into the biological growth plate scanner for automated detection and enumeration of bacterial growth. In other words, biological growth plate scanners automate the detection and enumeration of bacteria or other biological agents on a biological growth plate, and thereby improve the biological testing process by reducing human error.

SUMMARY

In general, the invention is directed to a biological growth plate scanner. The biological growth plate scanner may include a multi-color illumination system that illuminates the biological growth plate with different illumination colors. A monochromatic image capture device captures images of the biological growth plate during illumination of the growth plate with each of the illumination colors. A processor combines the images to form a composite multi-color image, and analyzes the composite image to produce an analytical result such as a colony count.

The biological growth plate scanner may include both front and back illumination components. The front illumination component provides illumination for a front side of the biological growth plate, which is scanned by the scanner. The back illumination component provides illumination for a back side of the biological growth plate. The back illumination component may include an optical diffuser element disposed behind the biological growth plate, e.g., under the biological growth plate when the major plane of the growth plate is oriented horizontally. The diffuser element receives light from one or more laterally disposed illumination sources, and distributes the light to illuminate a back side of the biological growth plate. The illumination sources in the front and back illumination components may take the form of light emitting diodes (LEDs) that can be controlled by the processor.

In one embodiment, the invention provides a device for scanning biological growth plates. The device comprises a multi-color illumination system that selectively illuminates a biological growth plate with different illumination colors, a monochromatic camera oriented to capture an image of the biological growth plate, and a processor that controls the camera to capture images of the biological growth plate during illumination with each of the different illumination colors.

In another embodiment, the invention provides a method for scanning biological growth plates. The method comprises selectively illuminating a biological growth plate with different illumination colors, and capturing images of the biological growth plate, using a monochromatic camera, during illumination with each of the different illumination colors.

In an added embodiment, the invention provides a system for scanning biological growth plates. The system comprises means for selectively illuminating a biological growth plate with different illumination colors, and means for capturing images of the biological growth plate, using a monochromatic camera, during illumination with each of the different illumination colors.

In a further embodiment, the invention provides a device for scanning biological growth plates. The device comprises a multi-color illumination system that selectively illuminates a biological growth plate with one or more different illumination colors, a camera oriented to capture an image of the biological growth plate, and a processor. The processor controls the camera to capture one or more images of the biological growth plate during illumination with each of the different illumination colors, and controls the illumination system to produce desired illumination intensities and illumination durations.

The invention can provide a number of advantages. For example, the use of a monochromatic camera results in resolution benefits and cost savings. In particular, a monochromatic camera offers increased spatial resolution relative to multi-color cameras and a resulting cost reduction per unit resolution. Rather than obtaining a single, multi-color image, the monochromatic camera captures multiple high resolution images, e.g., red, green and blue, and then combines them to produce a high resolution, multi-color image.

The use of different illumination colors can be achieved by independent sets of color LEDs, e.g., red, green and blue LEDs. The LEDs offer an extended lifetime relative to lamps and have inherently consistent output spectra and stable light output. A processor can control the LEDs to perform sequential illumination of the biological growth plates with different colors.

In addition, the color LEDs can be controlled independently to provide different output intensities and exposure durations. This feature is advantageous because the LEDs may exhibit different brightness characteristics, and reflector hardware or other optical components associated with the LEDs may present nonuniformities.

Also, the camera and associated lens, or different types of culture films, may exhibit different responses to the illumination colors. For example, the camera may be more or less sensitive to red, green and blue, presenting additional non-uniformities. However, the LED's can be independently controlled to compensate for such nonuniformities.

A back illumination component as described herein offers a convenient structure for effectively illuminating the back side of the biological growth plate with good uniformity while conserving space within the scanner. For example, the back illumination component may provide a diffuser element that serves to support a biological growth plate and distribute light injected into the diffuser element from laterally disposed illumination sources. In addition, the back illumination component may incorporate a set of fixed illumination sources that do not require movement during use, thereby alleviating fatigue to electrical wiring and reducing exposure to environmental contaminants.

Additional details of these and other embodiments are set forth in the accompanying drawings and the description below. Other features, objects and advantages will become apparent from the description and drawings, and from the claims.

DETAILED DESCRIPTION

The invention is directed to a biological growth plate scanner for biological growth plates. A biological growth plate can be presented to the biological growth plate scanner, which then generates an image of the plate and performs an analysis of the image to detect biological growth. For example, the scanner may count or otherwise quantify an amount of biological agents that appear in the image, such as a number of bacteria colonies. In this manner, the biological growth plate scanner automates the analysis of biological growth plates.

A biological growth plate scanner, in accordance with the invention, may include a multi-color illumination system that illuminates the biological growth plate with different illumination colors. A monochromatic image capture device captures images of the biological growth plate during illumination of the growth plate with each of the illumination colors. A processor combines the images to form a composite multi-color image, and analyzes the composite image and/or individual components of the composite image to produce an analytical result such as a colony count or presence/absence result.

In addition, the biological growth plate scanner may include both front and back illumination components. The back illumination component may include a diffuser element disposed under the biological growth plate. The optical diffuser element receives light from one or more laterally disposed illumination sources, and distributes the light to illuminate a back side of the biological growth plate. The illumination sources in the front and back illumination components may take the form of light emitting diodes (LEDs) that can be controlled by the processor. Various embodiments of a biological growth scanner will be described.

The invention may be useful with a variety of biological growth plates. For example, the invention may be useful with different plate-like devices for growing biological agents to enable detection and/or enumeration of the agents, such as thin-film culture plate devices, Petri dish culture plate devices, and the like. Therefore, the term "biological growth plate" will be used broadly herein to refer to a medium suitable for growth of biological agents to permit detection and enumeration of the agents by a scanner. In some embodiments, the biological growth plate can be housed in a cassette that supports multiple plates, e.g., as described in U.S. Pat. No. 5,573,950 to Graessle et al.

Figure 1:
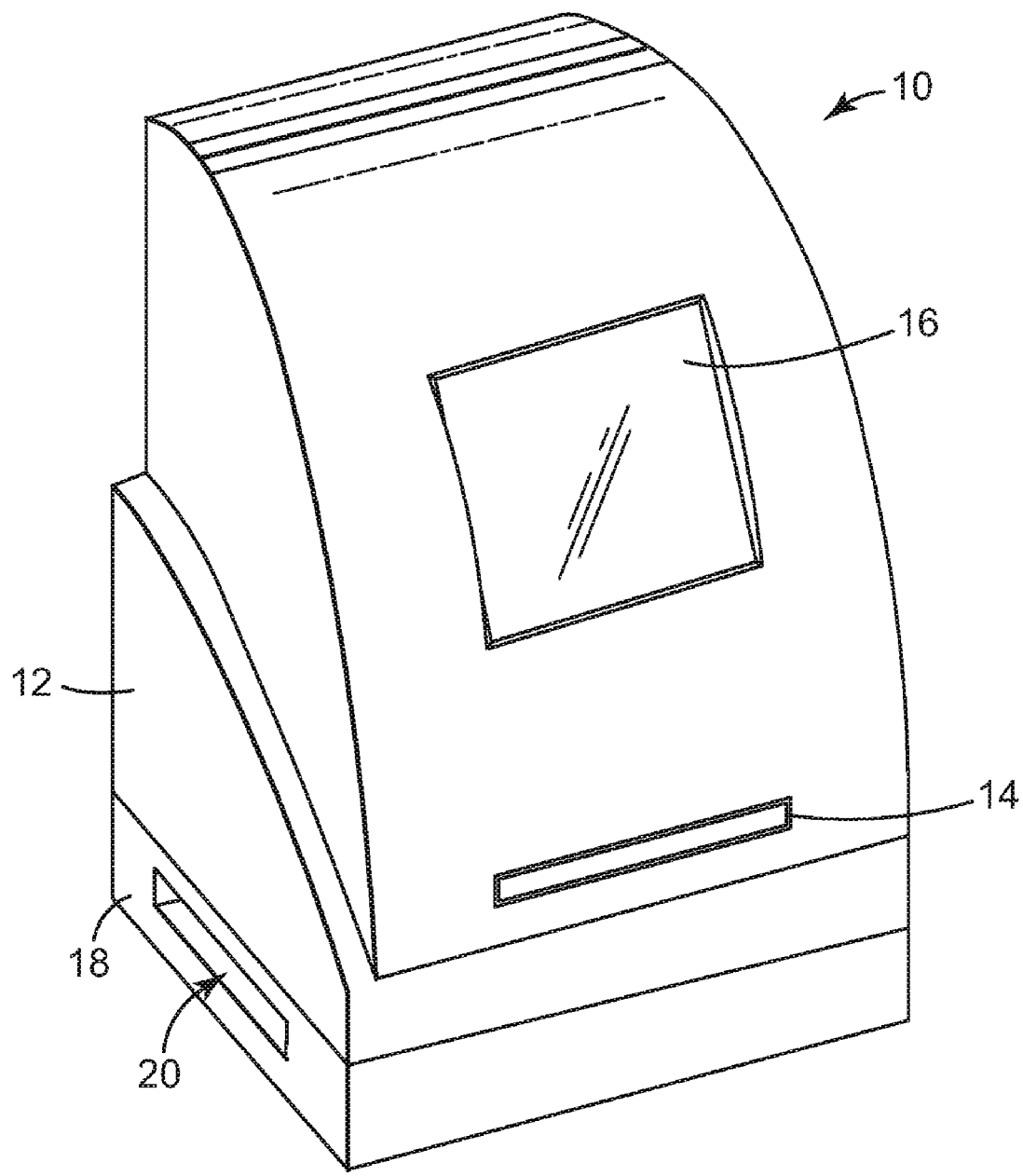
FIG. 1 is a perspective view of an exemplary biological growth plate scanner.

FIG. 1 is a perspective view of an exemplary biological growth plate scanner 10. As shown in FIG. 1, biological growth plate scanner 10 includes a scanner unit 12 having a drawer 14 that receives a biological growth plate (not shown in FIG. 1). Drawer 14 moves the biological growth plate into biological growth plate scanner 10 for scanning and analysis.

Biological growth plate scanner 10 also may include a display screen 16 to display the progress or results of analysis of the biological growth plate to a user. Alternatively or additionally, display screen 16 may present to a user an image of the growth plate scanned by biological growth plate scanner 10. The displayed image may be optically magnified or digitally scaled upward.

A mounting platform 18 defines an ejection slot 20 through which the growth plate can be ejected following analysis by biological growth plate scanner 10. Accordingly, biological growth plate scanner 10 may have a two-part design in which scanner unit 12 is mounted on mounting platform 18. The two-part design is depicted in FIG. 1 for purposes of example, and is not intended to be required by or limiting of the inventions described herein.

Scanner unit 12 houses an imaging device for scanning the biological growth plate and generating an image. The imaging device may take the form of a monochromatic line scanner or an area scanner, in combination with a multi-color illumination system to provide front and back illumination to the biological growth plate. In addition, scanner unit 12 may house processing hardware that performs analysis of the scanned image, e.g., in order to determine the number or amount of biological agents in the growth plate. For example, upon presentation of the biological growth plate via drawer 14, the plate may be positioned adjacent an optical platen for scanning When drawer 14 is subsequently opened, the growth plate may drop downward into the mounting platform 18 for ejection via ejection slot 20. To that end, mounting platform 18 may house a conveyor that ejects the growth plate from biological growth plate scanner 10 via ejection slot 20. After a biological growth plate is inserted into drawer 14, moved into scanner unit 12, and scanned, the biological growth plate drops downward into mounting platform 18, where a horizontal conveyor, such as a moving belt, ejects the plate via slot 20.

Figure 2:
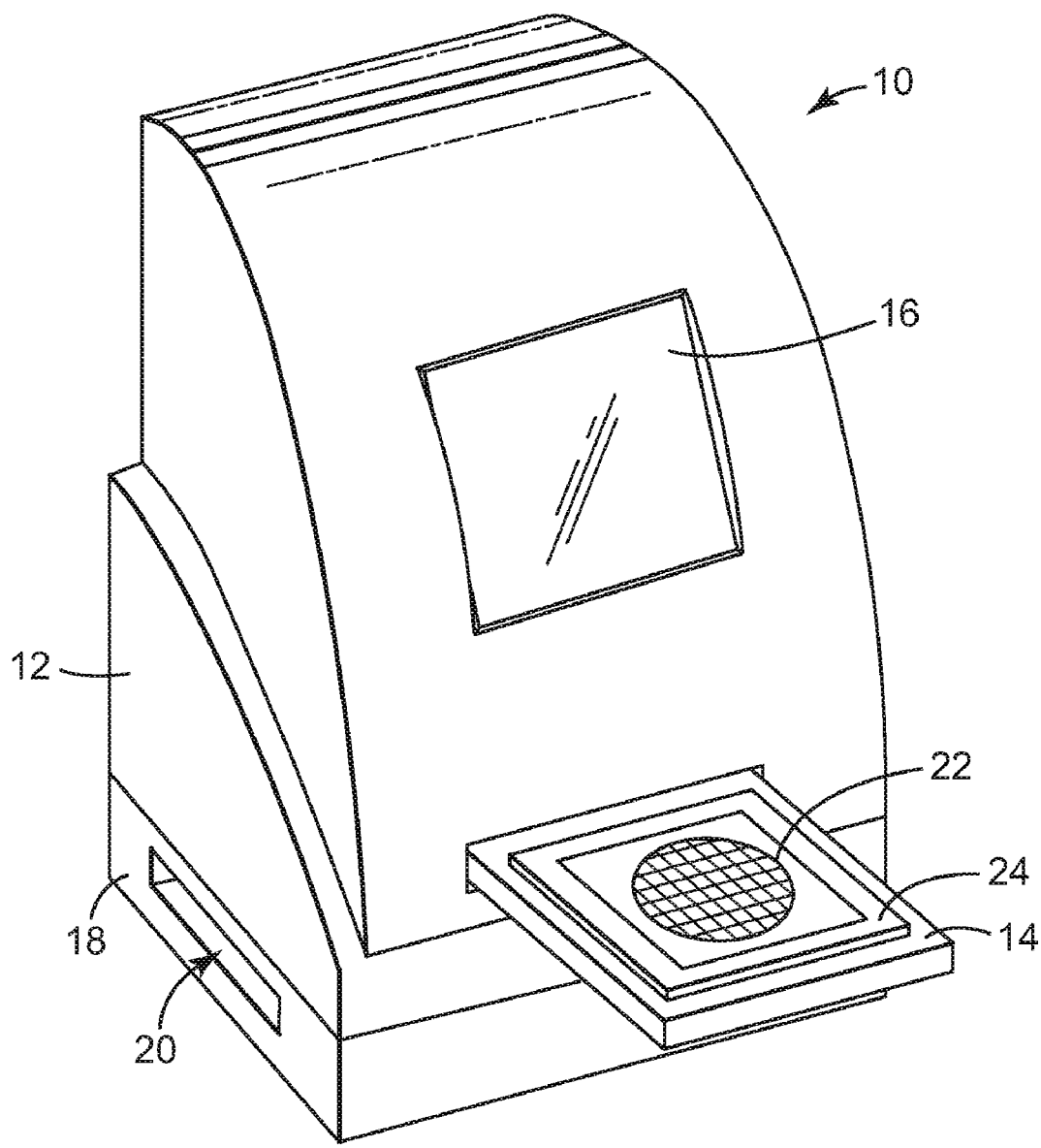
FIG. 2 is another perspective view of an exemplary biological growth plate scanner.

FIG. 2 is another perspective view of biological growth plate scanner 10. As shown in FIG. 2, drawer 14 extends outward from biological growth plate scanner 10 to receive a biological growth plate 22. As illustrated, a biological growth plate 22 may be placed on a platform 24 provided within drawer 14. In some embodiments, platform 24 may include positioning actuators such as cam levers to elevate the platform for precise positioning of growth plate 22 within biological growth plate scanner 10. Upon placement of biological growth plate 22 on platform 24, drawer 14 retracts into scanner unit 12 to place the biological growth plate in a scanning position, i.e., a position at which the biological growth plate is optically scanned.

Figure 3:
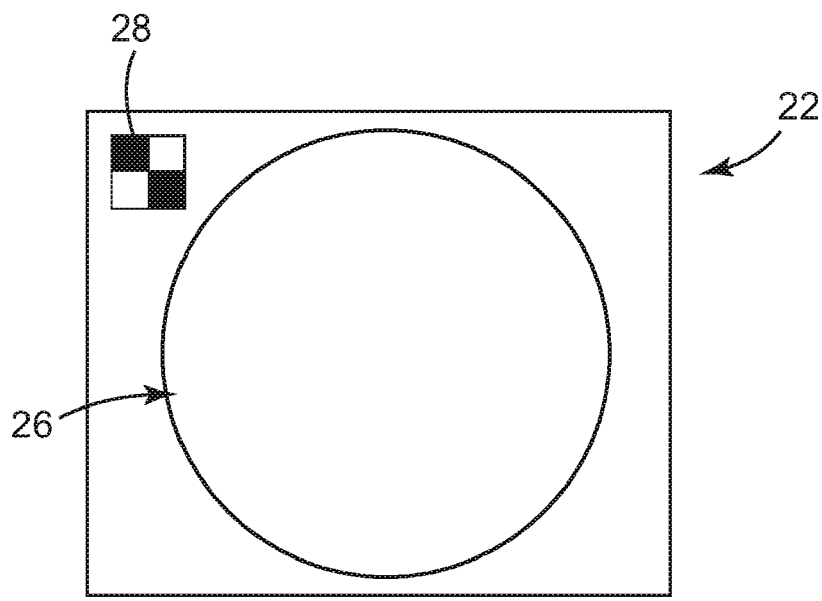
FIGS. 3 and 4 are front views of an exemplary growth plate bearing an indicator pattern for image processing profile selection.
Figure 4:
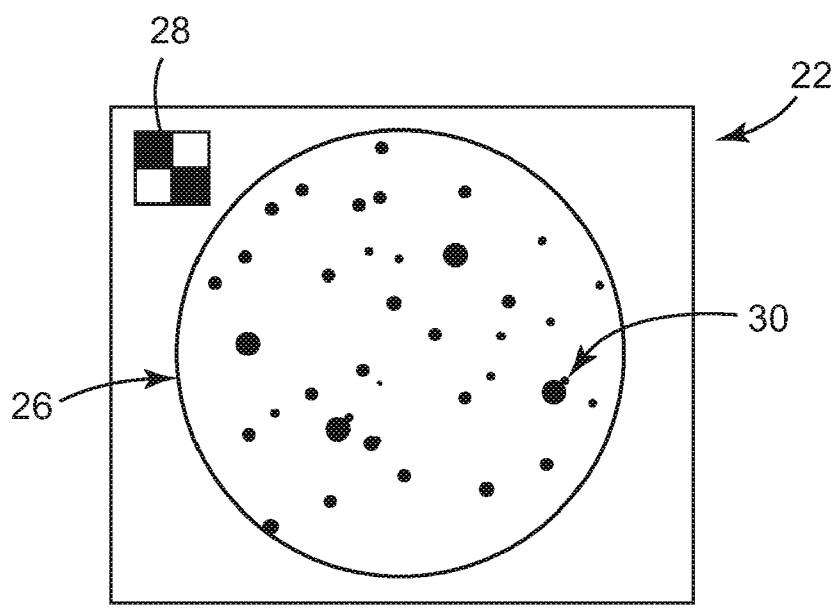

FIGS. 3 and 4 are front views of an exemplary biological growth plate 22. By way of example, a suitable growth plate 22 may comprise biological growth plates sold by 3M under the trade name PETRIFILM plates. Alternatively, biological growth plate 22 may comprise other biological growth media for growing particular bacteria or other biological agents. In some embodiments, biological growth plate 22 may carry a plate type indicator 28 to facilitate automated identification of the type of biological media associated with the growth plate.

Plate type indicator 28 presents an encoded pattern that is machine-readable. In the example of FIGS. 3 and 4, plate type indicator 28 takes the form of an optically readable pattern. In particular, FIGS. 3 and 4 depict a four-square pattern of light and dark quadrants formed in a corner margin of biological growth plate 22. In other words, plate type indicator 28 defines a two-dimensional grid of cells modulated between black and white to form an encoded pattern.

A wide variety of optical patterns such as characters, bar codes, two-dimensional bar codes, optical gratings, holograms and the like are conceivable. In addition, in some embodiments, plate type indicator 28 may take the form of patterns that are readable by magnetic or radio frequency techniques. Alternatively, plate type indicator 28 may take the form of apertures, slots, surface contours, or the like that are readable by optical or mechanical techniques. In each case, plate type indicator 28 carries information sufficient to enable automated identification of the type of biological growth plate 22 by biological growth plate scanner 10.

Biological growth plates may facilitate the rapid growth and detection and enumeration of bacteria or other biological agents including, for example, aerobic bacteria, *E. coli*, coliform, enterobacteriaceae, yeast, mold, *Staphylococcus aureus, Listeria, Campylobacter* and the like. The use of PETRIFILM plates, or other growth media, can simplify bacterial testing of food samples. Moreover, biological growth plate scanner 10 can further simplify such testing by providing automated plate type detection, and automated selection of image processing profiles based on the detected plate type to analyze biological growth plate 22, e.g., by counting bacterial colonies on an image of the plate.

As shown in FIG. 3, biological growth plate 22 defines a growth area 26. A determination of whether a given sample being tested in plate 22 is acceptable, in terms of bacterial colony counts, may depend on the number of bacterial colonies per unit area. Accordingly, scanner 10 quantifies the amount of bacterial colonies per unit area on plate 22, and may compare the amount, or "count," to a threshold. The surface of biological growth plate 22 may contain one or more growth enhancing agents designed to facilitate the rapid growth of one or more types of bacteria or other biological agents.

After placing a sample of the material being tested, typically in liquid form, on the surface of biological growth plate 22 within growth area 26, plate 22 can be inserted into an incubation chamber (not shown). In the incubation chamber, bacterial colonies or other biological agents being grown by growth plate 22 manifest themselves, as shown in biological growth plate 22 of FIG. 4. The colonies, represented by various dots 30 on biological growth plate 22 in FIG. 4, may appear in different colors on plate 22, facilitating automated detection and enumeration of bacterial colonies by scanner 10.

Figure 5:
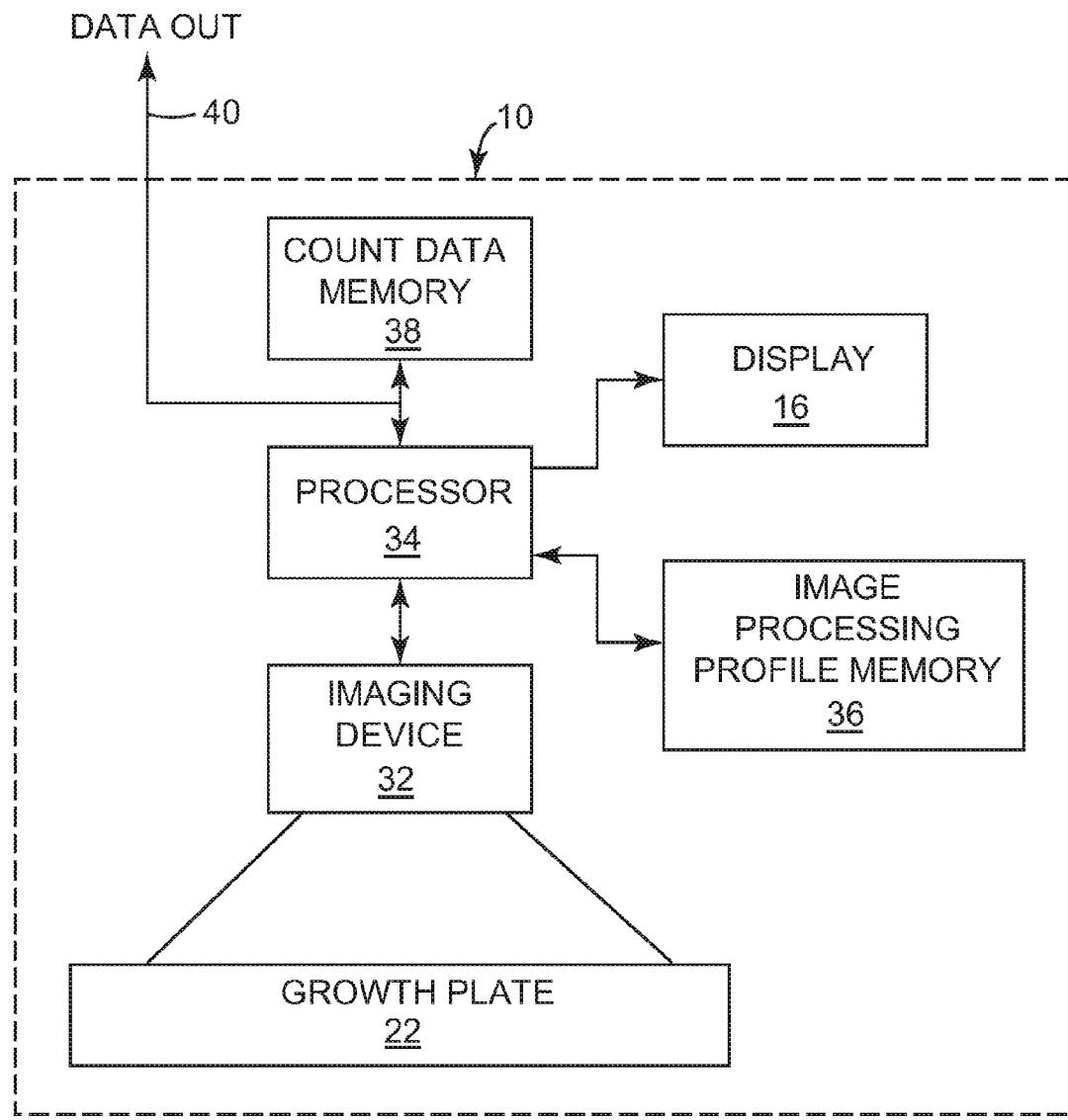
FIG. 5 is a block diagram illustrating internal operation of a biological growth plate scanner.

FIG. 5 is a block diagram illustrating internal operation of a biological growth plate scanner 10. As illustrated in FIG. 5, a biological growth plate 22 is positioned within biological growth plate scanner 10 on a platform (not shown in FIG. 5). The platform places biological growth plate 22 at a desired focal plane of an imaging device 32. In accordance with the invention, imaging device 32 may include multi-color illumination systems for front and back illumination of growth plate 22, as well as a monochromatic line or area scanner that captures an image of the surface of growth plate 22. In some embodiments, for example, imaging device 32 may take the form of a two-dimensional, monochromatic camera.

In general, imaging device 32 captures images of biological growth plate 22, or at least a growth region within the biological growth plate, during illumination of the biological growth plate with one or more different illumination colors. In some embodiments, illumination durations and illumination intensities may be controlled according to requirements of different biological growth plates. In addition, selective illumination of a first side and a second side of the biological growth plate can be controlled according to requirements of different biological growth plates.

A processor 34 controls the operation of imaging device 32. In operation, processor 34 controls imaging device 32 to illuminate biological growth plate 22 with different illumination colors, and capture images of biological growth plate 22. Processor 34 receives image data representing the scanned images from imaging device 32 during illumination with each of the different illumination colors, and combines the images to form a multi-color composite image. Processor 34 analyzes the composite image of biological growth plate 22 and analyzes the image to produce an analytical result, such as a colony count or a presence/absence result.

In some embodiments, processor 34 may extract or segregate a portion of the image to isolate plate type indicator 28. Using machine vision techniques, for example, processor 34 may analyze plate type indicator 28 to identify a plate type associated with biological growth plate 22. Processor 34 then retrieves an image processing profile from image processing profile memory 36. The image processing profile corresponds to the detected plate type, and may specify image capture conditions and image analysis conditions. Processor 34 may take the form of a microprocessor, digital signal processor, application specific integrated circuit (ASIC), field programmable gate array (FPGA) or other integrated or discrete logic circuitry programmed or otherwise configured to provide functionality as described herein.

Using the image processing profile, processor 34 loads appropriate image processing parameters and proceeds to process the scanned image of biological growth plate 22. In this manner, processor 34 forms an image processing device in the sense that it processes the image data obtained from biological growth plate 22. The image processing parameters may vary with the image processing profile and detected plate type, and may specify particular imager analysis conditions, including parameters such as color, size, shape and proximity criteria for analysis of the scanned image. The criteria may differ according to the type of plate 22 to be analyzed, and may significantly affect colony count or other analytical results produced by biological growth plate scanner 10. The image processing profile also may specify image capture conditions such as illumination colors, intensities, and durations suitable for a particular type of biological growth plate. Suitable techniques for plate type identification and use of image processing profiles are further described in commonly assigned U.S. Pat. No. 7,298,885, entitled "BIOLOGICAL GROWTH PLATE SCANNER WITH AUTOMATED IMAGE PROCESSING PROFILE SELECTION," the entire content of which is incorporated herein by reference.

Upon selection of the appropriate image processing parameters, processor 34 processes the scanned image and produces an analytical result, such as a colony count or a presence/absence result, which is presented to a user via display 16. Processor 34 also may store the analytical result in memory, such as count data memory 38, for later retrieval from scanner 10. The data stored in count data memory 38 may be retrieved, for example, by a host computer that communicates with biological growth plate scanner 10 via a communication port 40, e.g., a universal serial bus (USB) port. The host computer may compile analytical results for a series of biological growth plates 22 presented to biological growth plate scanner 10 for analysis.

Automated selection of image processing profiles within biological growth plate scanner 10 can provide a convenient and accurate technique for selecting the appropriate image processing profile. Automated selection of image processing profiles can promote the accuracy of bacterial colony counts and other analytical procedures. In particular, automatic image processing profile selection can avoid the need for a technician to visually identify and manually enter the plate type. In this manner, plate identification errors sometimes associated with human intervention can be avoided. Consequently, the combination of a scanner 10 and a biological growth plate 22 that carries plate type indicator 28 can promote efficiency and workflow of laboratory technicians while enhancing analytical accuracy and, in the end, food safety and human health.

Figure 6:
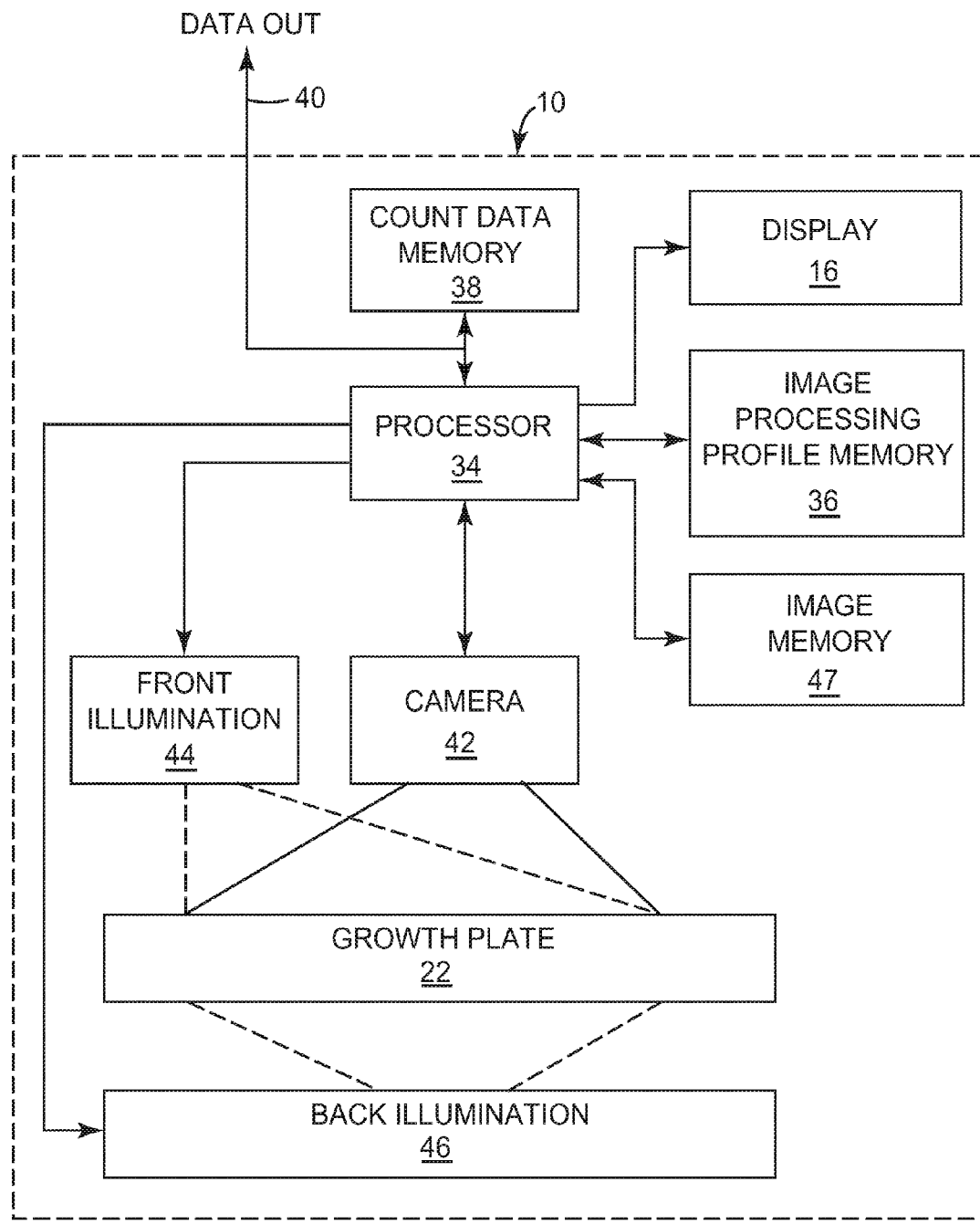
FIG. 6 is a block diagram illustrating the biological growth plate scanner of FIG. 5 in greater detail.

FIG. 6 is a block diagram illustrating biological growth plate scanner 10 of FIG. 5 in greater detail. Imaging device 32 (FIG. 5) of biological growth plate scanner 10 may include, as shown in FIG. 6, a camera 42, front illumination component 44 and back illumination component 46. In accordance with the invention, front and back illumination systems 44, 46 may produce different illumination intensities, colors and durations on a selective basis. In particular, processor 34 controls front and back illumination systems 44, 46 to expose biological growth plate 22 to different illumination colors, intensities and durations. In addition, processor 34 controls camera 42 to capture images of biological growth plate 22 during illumination with the different colors.

For example, processor 34 may provide coordinated control of illumination systems 44, 46 and camera 42 to capture multiple images of biological growth plate 22. Processor 34 then combines the multiple images to form a multi-color, composite image. Using the multi-color, composite image, and/or individual components of the composite image, processor 34 analyzes biological growth plate 22 to produce an analytical result such as a detection or colony count. In one embodiment, front and back illumination systems 44, 46 may expose biological growth plate 22 to red, green and/or blue illumination colors on a selective basis under control of processor 34. In this example, camera 42 captures red, green and blue images of biological growth plate 22. Processor 34 then combines the red, green and blue images to form the multi-color, composite image for analysis.

As an illustration, processor 34 may first activate red illumination sources within front and back illumination components 44, 46 to expose biological growth plate 22 to red illumination. In particular, processor 34 may control the intensity and exposure duration of the red illumination sources. In synchronization with the red illumination exposure, camera 42 captures a red image of biological growth plate 22 and stores the captured image in an image memory 47 within scanner 10.

Processor 34 then activates green illumination sources within front and back illumination components 44, 46 to expose biological growth plate 22 to green illumination, followed by capture of a green image by camera 42. Similarly, processor activates blue illumination sources within front and back illumination components 44, 46 to expose biological growth plate 22 to blue illumination, followed by capture of a blue image by camera 42.

Camera 42 captures monochromatic images for each of the red, green and blue illumination exposures, and may store the images in separate files. Using the files, processor 34 combines the captured images to form the composite image for analysis. The order in which biological growth plate 22 is exposed to the multiple illumination colors may vary. Therefore, exposure to red, green and blue illumination sources in sequence should not be considered limiting of the invention.

The individual images captured by camera 42 may be represented in terms of optical intensity or optical density. In other words, camera 42 captures gray scale data that can be used to quantify the reflected output of biological growth plate 22 for each exposure channel, e.g., red, green and blue. The use of a monochromatic camera 42 to capture the individual images can result in image resolution benefits and cost savings. In particular, a less expensive monochromatic camera 42 may offer increased spatial resolution relative to multi-color cameras that capture red, green and blue spectra simultaneously. Accordingly, camera 42 can obtain high resolution imagery needed for effective analysis of biological growth plate 22 with reduced cost. Rather than obtain a single, multi-color image monochromatic camera 42 captures multiple high resolution images, e.g., red, green and blue, and then processor 34 combines them to produce a high resolution, multi-color image.

The different illumination sources within front and back illumination systems 44, 46 may take the form of LEDs. In particular, the different illumination colors can be achieved by independent sets of color LEDs, e.g., red, green and blue LEDs. As an advantage, LEDs offer an extended lifetime relative to other illumination sources such as lamps. LEDs also may provide inherently consistent output spectra and stable light output.

Also, processor 34 can readily control the output intensities and exposure durations of the LEDs to perform sequential illumination of the biological growth plates 22 with appropriate levels of illumination. Processor 34 can be programmed to control the different sets of color LEDs independently to provide different output intensities and exposure durations for each illumination color applied to biological growth plate 22.

This ability to independently control the LEDs via processor 34 can be advantageous because the LEDs may exhibit different brightness characteristics, and reflector hardware or other optical components associated with the LEDs may present nonuniformities. In addition, camera 42 and one or more associated camera lenses may exhibit different responses to the illumination colors. For example, camera 42 may be more or less sensitive to red, green and blue, presenting additional nonuniformities in the color response for a given illumination channel.

Processor 34 can independently control the LEDs, however, in order to compensate for such nonuniformities. For example, scanner 10 may be calibrated at the factory or in the field to characterize the response of camera 42 to the different illumination sources, and then compensate the response by storing appropriate drive values to be applied by processor 34. Hence, processor 34 may apply different drive values to the LEDs for different illumination colors and intensity levels to produce a desired degree of uniformity in the images captured by camera 42.

In some embodiments, scanner 10 may process images of different biological growth plates 22 according to different image processing profiles. The image processing profiles may be selected by processor 34 based on user input or identification of the type of biological growth plate 22 presented to scanner 10. The image processing profile may specify particular image capture conditions, such as illumination intensities, exposure durations, and colors, for capturing images of particular plate types. Thus, the scanner may apply different image capture conditions, including different illumination conditions, in processing images of different biological growth plates 22.

As an illustration, some types of biological growth plates 22 may require illumination with a particular color, intensity and duration. In addition, some biological growth plates 22 may require only front or back illumination, but not both. For example, an aerobic count plate may require only front illumination as well as illumination by only a single color such as red. Alternatively, an *E. coli*/Coliform plate may require only back illumination and a combination of red and blue illumination. Similarly, particular intensity levels and durations may be appropriate. For these reasons, processor 34 may control illumination in response to image capture conditions specified by an image processing profile.

Figure 7:
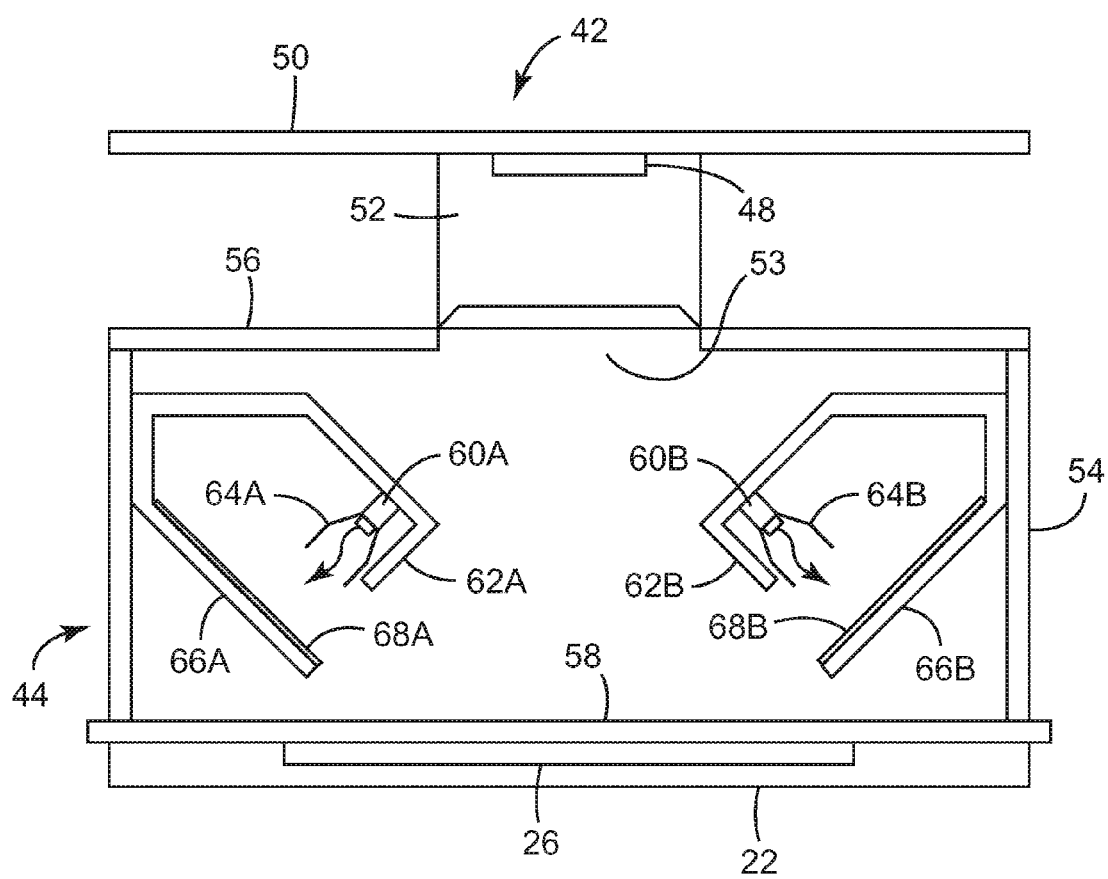
FIG. 7 is a side view illustrating a front illumination component for a biological growth plate scanner.

FIG. 7 is a side view illustrating a front illumination component 44 for biological growth plate scanner 10. As shown in FIG. 7, front illumination component 44 may be integrated with camera 42. For example, camera 42 may include a camera body with a CMOS or CCD camera chip 48 mounted to a camera backplane 50, such as a printed circuit board, which may carry circuitry to drive camera chip 48 and receive image data for processor 34. A camera lens 52 may be oriented to capture images of a biological growth plate 22 via an aperture 53 in a housing defined by front illumination component 44. In the example of FIG. 7, front illumination component 44 includes a side wall 54, a front wall 56, and an optical platen 58. Optical platen 58 may simply be a transparent sheet of glass or plastic that permits transmission of illuminating light and capture of imagery from biological growth plate 22 by camera 42. In some embodiments, optical platen 58 may be eliminated such that the growth area 26 of plate 22 is illuminated with no intervening structure between growth area 26 and the emitted light. Biological growth plate 22 may be elevated into contact or close proximity with optical platen 58 to permit camera 42 to capture images.

A number of components may be housed within front illumination component 44. For example, front illumination component 44 may include one or more illumination sources 60A, 60B, preferably arranged in linear arrays about a periphery of growth area 26 of biological growth plate 22. In particular, a linear array of red, green and blue illumination sources 60A, 60B may extend along each of four edges of biological growth plate 22, e.g., in a square pattern. In other embodiments, the illumination sources may be arranged in alternative patterns, e.g., circular patterns. Again, illumination sources 60A, 60B may take the form of LEDs and may be arranged in groups of one red, one green and one blue LED.

Illumination sources 60A, 60B may be mounted within illumination chambers 62A, 62B. Reflective cowels 64A, 64B are mounted about illumination sources 60A, 60B and serve to reflect and concentrate the light emitted by the illumination sources toward inwardly extending walls 66A, 66B of chambers 62A, 62B. The reflective material may be coated, deposited, or adhesively affixed to an interior surface of reflective cowels 64A, 64B. An example of a suitable reflective material for reflective cowels 64A, 64B is the 3M Radiant Mirror Reflector VM2000 commercially available from 3M Company of St. Paul, Minn.

Walls 66A, 66B may carry a diffusing material such as an optical diffusing film 68A, 68B that serves to diffuse light received from illumination sources 60A, 60B. The diffuse light is transmitted into an interior chamber of front illumination component 44 to illuminate growth region 26 of biological growth plate 22. An example of a suitable diffusing material for diffusing film 68A, 68B is the Mitsui WS-180A diffuse white film, commercially available from Mitsui & Co., Inc., of New York, N.Y. The diffusing film 68A, 66B may be coated or adhesively affixed to an interior surface of walls 66A, 66B.

Figure 8:
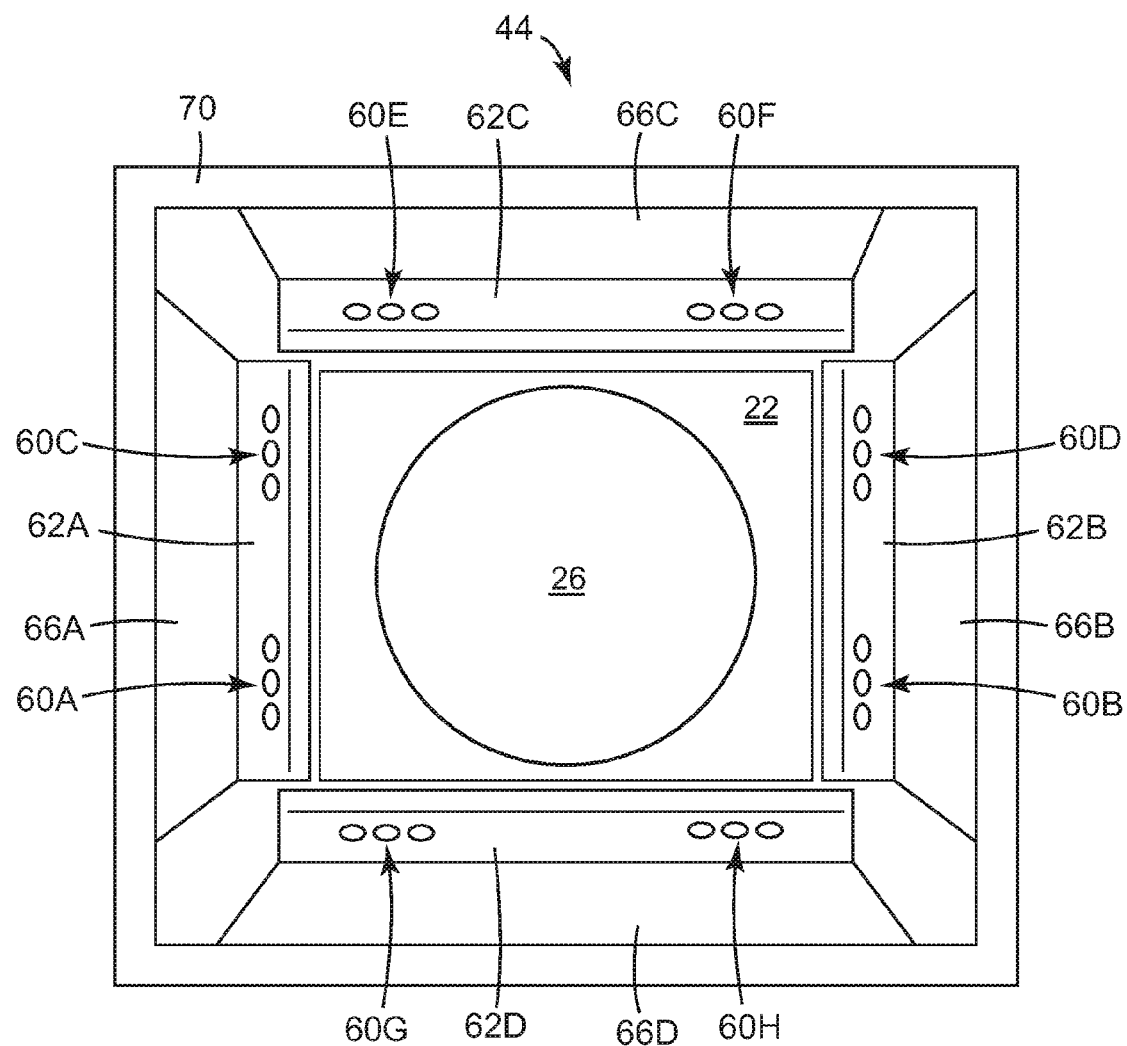
FIG. 8 is a front view illustrating a front illumination component for a biological growth plate scanner.

FIG. 8 is a front view illustrating front illumination component 44 in greater detail. As shown in FIG. 8, front illumination component 44 may include four illumination chambers 62A, 62B, 62C, 62D arranged around a periphery of biological growth plate 22. Each illumination chamber 62 may include two sets of illumination sources 60. For example, chamber 62A may contain illumination sources 60A, 60C, chamber 62B may contain illumination sources 60B, 60D, chamber 62C may contain illumination sources 60E, 60F, and chamber 62D may contain illumination sources 60G, 60H. In addition, chambers 62A, 62B, 62C, 62D may include respective walls 66A, 66B, 66C, 66D carrying diffusing film. In other embodiments, each respective chamber 62 may include any number of illumination sources 60, which may or may not be the same number of illumination sources in other chambers.

Illumination sources 60 may include an array of illumination elements grouped together, e.g., in groups of three. In particular, each illumination source 60 may include a red LED, a green LED, and a blue LED that can be separately activated to illuminate biological growth plate 22. Upon activation of the individual LEDs, an inner chamber defined by front illumination component 44 is filled with diffused light to provide front illumination to biological growth plate 22. Camera 42 captures an image of biological growth plate 22 during successive exposure cycles with each of the different illumination colors.

Figure 9:
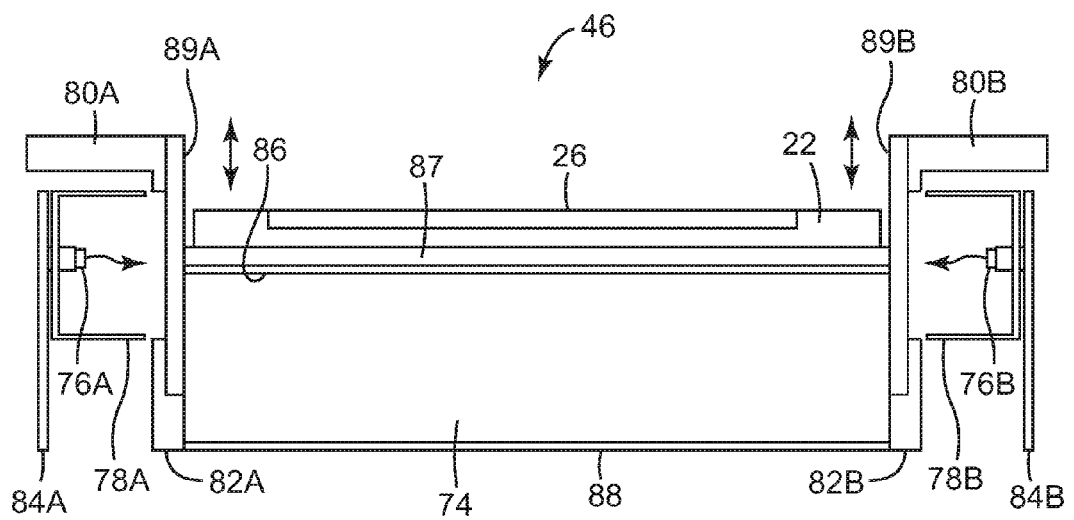
FIG. 9 is a side view illustrating a back illumination component for a biological growth plate scanner in a loading position.

FIG. 9 is a side view illustrating back illumination component 46 for a biological growth plate scanner 10 in a loading position, i.e., a position in which biological growth plate 22 is initially loaded into the scanner. In some embodiments, biological growth plate 22 may be loaded into scanner via drawer 14, as shown in FIG. 2. In particular, drawer 14 carries a diffuser element 74 that serves as a platform for biological growth plate 22. Drawer 14 may be configured to permit retraction of biological growth plate 22 into the interior of scanner 10, and elevation of the biological growth plate into a scanning position.

Once loaded, biological growth plate 22 can be supported by optical diffuser element 74 or, alternatively, supported by a transparent platform in close proximity to the optical diffuser element. Optical diffuser element 74 serves to diffuse light that is laterally injected into the diffuser element and radiate the light upward to provide back side illumination of biological growth plate 22. Back illumination component 46 effectively illuminates the back side of biological growth plate 22 with good uniformity while conserving space within scanner 10.

In addition, back illumination component 46 incorporates a set of fixed illumination sources 76A, 76B that do not require movement during use, thereby alleviating fatigue to electrical wiring and reducing exposure to environmental contaminants. Rather, biological growth plate 22 and diffuser element 74 are elevated into position in alignment with the fixed illumination sources 76A, 76B. In summary, back illumination component 46 offers good illumination uniformity across the surface of biological growth plate 22, a flat illumination surface, a fixed arrangement of illumination sources 76A, 76B, and an efficient size and volume for space conservation.

Illumination sources 76A, 76B are positioned adjacent a lateral edge of diffuser element 74, when the diffuser element occupies the elevated, scanning position. Each illumination source 76A, 76B may include a reflector cowl 78A, 78B to reflect and concentrate light emitted by the illumination sources toward respective edges of diffuser element 74. In this manner, illumination sources 76A, 76B inject light into optical diffuser element 74. The reflective material may be coated, deposited, or adhesively affixed to an interior surface of reflective cowels 78A, 78B. An example of a suitable reflective material for reflective cowels 78A, 78B is the 3M Radiant Mirror Reflector VM2000 commercially available from 3M Company of St. Paul, Minn.

A platen support 80A, 80B may be provided to support an optical platen 58 (FIG. 7), and provide an interface for engagement of back illumination component 46 with front illumination component 44. As further shown in FIG. 9, a support bracket 82A, 82B provides a mount for optical diffuser element 74. In addition, illumination sources 76A, 76B are mounted to backplanes 84A, 84B, which may carry a portion of the circuitry necessary to drive the illumination sources. However, backplanes 84A, 84B and illumination sources 76A, 76B may be generally fixed so that travel of the illumination sources and associated fatigue to wiring and other electrical components is not necessary, and exposure to environmental contaminants is reduced.

A back side of diffuser element 74 may be defined by a reflective film 88 that promotes inner reflection of light received from illumination sources 76A, 76B, i.e., reflection of light into an interior chamber defined by diffuser element. In this manner, the light does not exit the back region of diffuser element 74, but rather is reflected inward and upward toward biological growth plate 22. Reflective film 88 may be coated, deposited, or adhesively bonded to a wall defined by diffuser element 74. Alternatively, reflective film 88 may be free-standing and define the back wall of diffuser element 74. An example of a suitable material for reflective film 88 is 3M Radiant Mirror Film, 2000F1A6, commercially available from 3M Company of St. Paul, Minn.

A front side of diffuser element 74, adjacent biological growth plate 22, may carry an optical diffusing material such as an optical light guide and diffusing film 86. Diffuser element 74 may define an internal chamber between reflective film 88, optical light guide and diffusing film 86, and respective light transmissive layers 89A, 89B forming side walls adjacent illumination sources 76A, 76B. As will be described, opposing side walls of optical diffuser element 74 on sides not adjacent illumination sources 76A, 76B may be formed by reflective layers to promote internal reflection of light injected into the diffuser element.

The internal chamber defined by optical diffuser element 74 may simply be empty and filled with air. Optical light guide and diffusing film 86 serves to diffuse light emitted from diffuser element 74 toward biological growth plate 22. An example of a suitable optical diffusing film is 3M Optical Lighting Film, printed with a pattern of diffuse white dots having 30% area coverage, with prism orientation facing down toward the diffuser element. In particular, the prisms of optical light guide and diffusing film 86 face into diffuser element 74 and the orientation of the prisms is generally perpendicular to illumination sources 76A, 76B. The 3M Optical Lighting Film is commercially available from 3M Company of St. Paul, Minn.

In addition, diffuser element 74 may include a scratch-resistant, light transmissive layer 87 over optical light guide and diffusing film 86. Biological growth plate 22 may be placed in contact with scratch-resistant layer 87. Additional scratch-resistant, light transmissive layers 89A, 89B may be disposed adjacent the lateral edges of diffuser element 74. In particular, layers 89A, 89B may be disposed between illumination sources 76A, 76B and diffuser element 74.

Scratch-resistant, light transmissive layers 89A, 89B are placed over light entry slots at opposite sides of diffuser element 74 to permit transmission of light from illumination sources 76A, 76B into the diffuser element, and also provide a durable surface for upward and downward sliding movement of the diffuser element. An example of a suitable scratch-resistant, light transmissive material for use as any of layers 87, 89A, 89B resides in the class of acrylic glass-like materials, sometimes referred to as acrylglass or acrylplate. Alternatively, layers 87, 89A, 89B may be formed by glass.

An acrylic or glass plate as layer 87 can be used to provide a stable, cleanable platform for the biological growth plate, and protect diffuser element 74 from damage. An approximately 1 mm gap may be provided between layer 87 and optical light guide and diffusing film 86 to preserve the optical performance of the diffusing film, which could be altered by contact with materials other than air.

Figure 10:
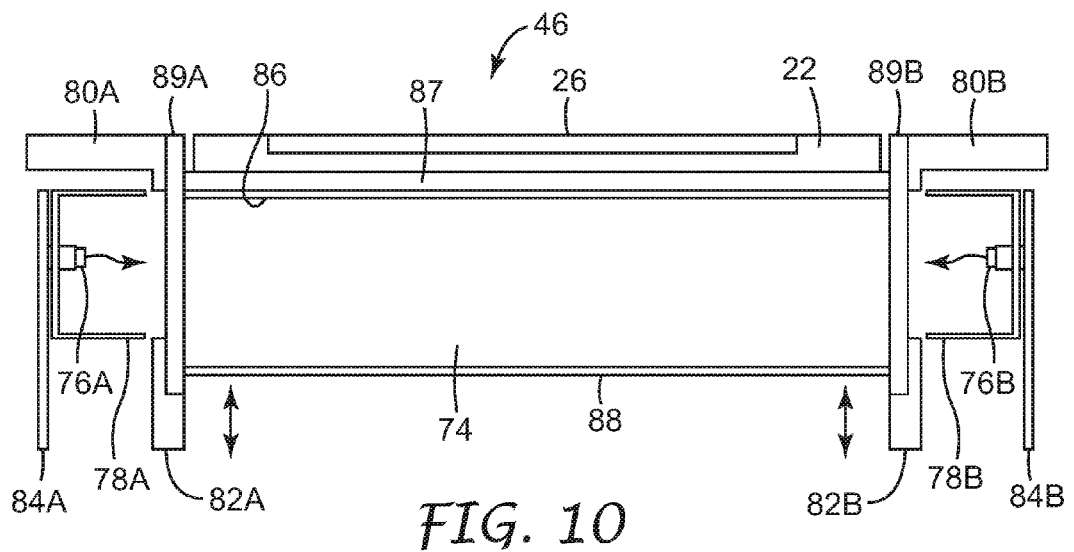
FIG. 10 is a side view illustrating the back illumination component of FIG. 9 in a scanning position.

FIG. 10 is a side view illustrating the back illumination component 46 of FIG. 9 in a scanning position. In particular, in FIG. 10, diffuser element 74 is elevated relative to the position illustrated in FIG. 9. Diffuser element 74 may be elevated by a variety of elevation mechanisms, such as camming, lead screw or pulley arrangements. As diffuser element 74 is elevated into scanning position, biological growth plate 22 is placed in proximity or in contact with optical platen 58 (FIG. 7).

Upon elevation into scanning position, illumination sources 76A, 76B inject light into diffuser element 74, which diffuses the light and directs it upward to provide back illumination for biological growth plate 22. As will be described, illumination sources 76A, 76B may incorporate differently colored illumination elements that are selectively activated to permit camera 42 to separate monochromatic images for each color, e.g., red, green and blue.

Figure 11:
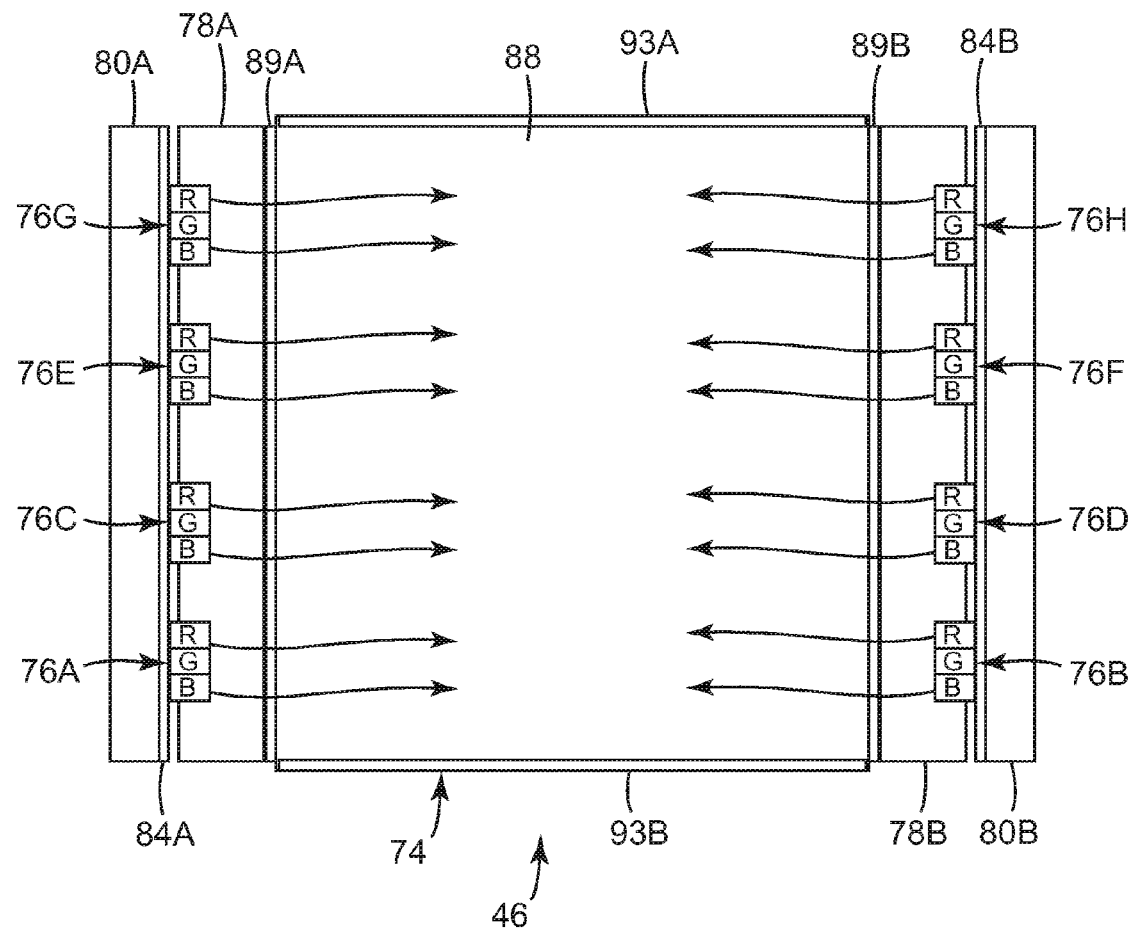
FIG. 11 is a bottom view illustrating the back illumination component of FIGS. 9 and 10.

FIG. 11 is a bottom view illustrating back illumination component 46 of FIGS. 9 and 10. As shown in FIG. 11, multiple illumination sources 76A-76H may be disposed in linear arrays on opposite sides of diffuser element 74. FIG. 11 provides a perspective of back illumination components from a side opposite biological growth plate 22, and therefore shows reflective layer 88. Each illumination source 76 may include three illumination elements, e.g., a red (R) element, a green (G) element, and a blue (B) element. The red, green and blue elements may be red, green and blue LEDs. Back illumination component 46 may be configured such that all red elements can be activated simultaneously to illuminate the back side of biological growth plate 22 with red light in order to capture a red image with camera 42. The green elements and blue elements, respectively, may be similarly activated simultaneously.

As further shown in FIG. 11, reflective layers 93A, 93B form opposing side walls of diffuser element 74 on sides not adjacent illumination sources 76. Reflective layers 93A, 93B may be formed from materials similar to reflective layer 88, and may be affixed to interiors or respective side walls or form free-standing walls themselves. In general, reflective layers 88, 93A, 93B serve to reflect light injected by illumination sources 76 into the interior chamber defined by diffuser element 74, preventing the light from escaping from the back side or side walls of the diffuser element. Instead, the light is reflected inward and toward diffusing material 86. In this manner, the light is concentrated and then diffused by diffusing material 86 for transmission to illuminate a back side of biological growth plate 22.

Figure 12:
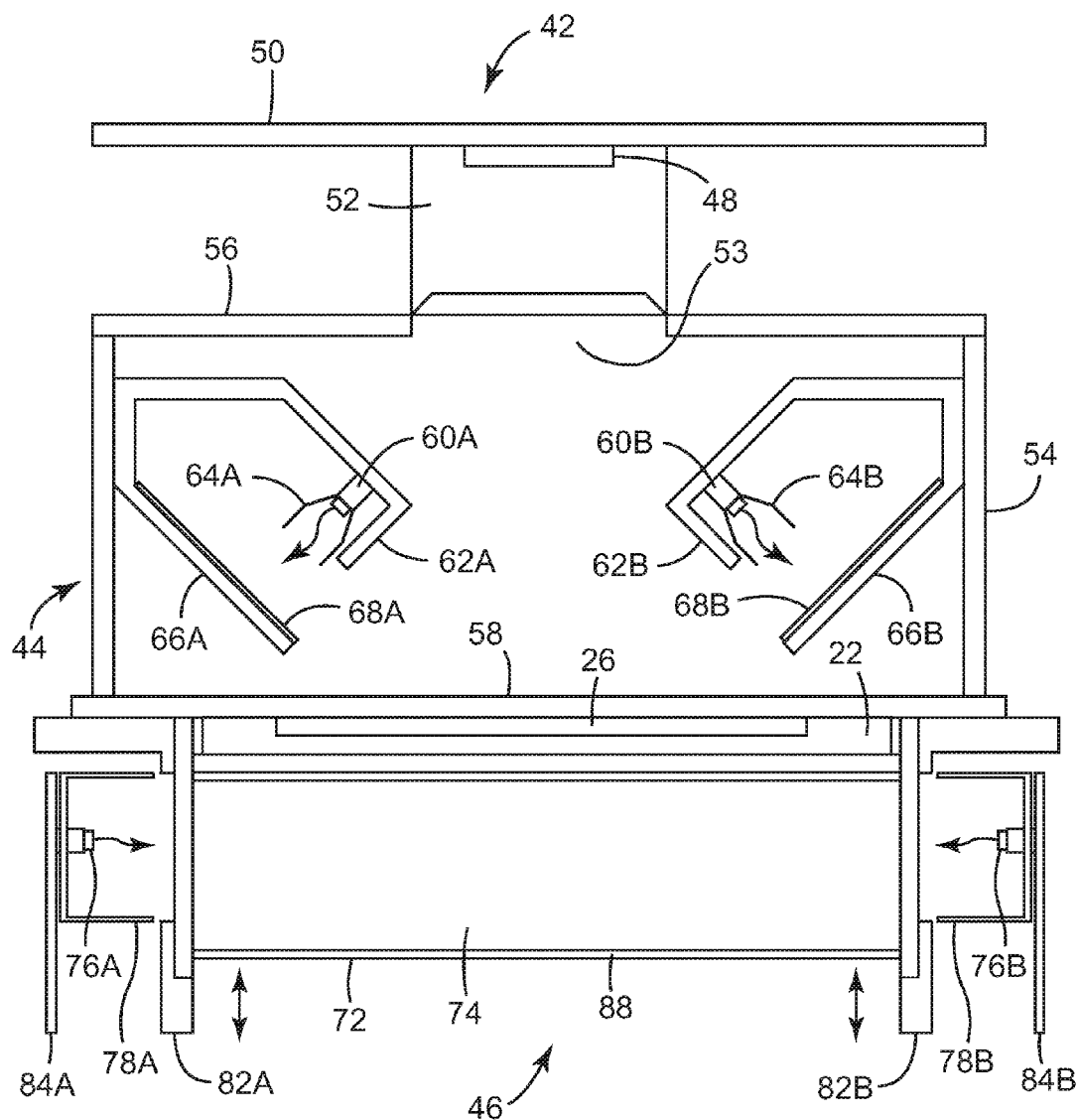
FIG. 12 is a side view illustrating the combination of front and back illumination components for a biological growth plate scanner.

FIG. 12 is a side view illustrating the combination of front and back illumination components 44, 46, as well as camera 42, for biological growth plate scanner 10. As shown in FIG. 12, optical platen 58 serves as an interface between front illumination component 44 and back illumination component 46. In operation, biological growth plate 22 is elevated into proximity or contact with optical platen 58. Front and back illumination components 44, 46 then selectively expose biological growth plate 22 with different illumination colors to permit camera 42 to capture images of the biological growth plate. For example, front and back illumination component 44, 46 may selectively activate red, green and blue LEDs in sequence to form red, green and blue images of biological growth plate 22.

Figure 13:
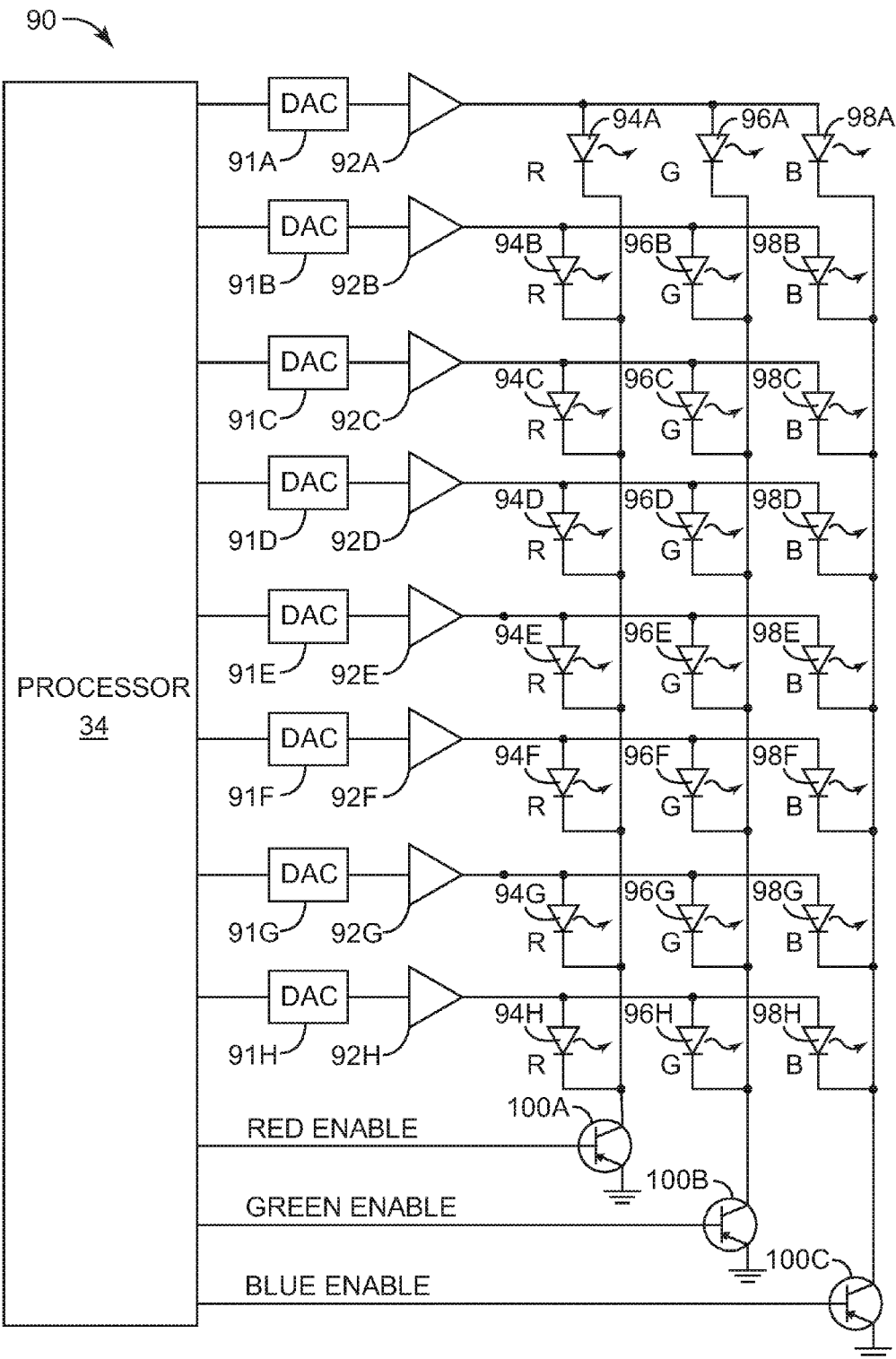
FIG. 13 is a circuit diagram illustrating a control circuit for an illumination system.

FIG. 13 is a circuit diagram illustrating a control circuit 90 for an illumination system. Control circuit 90 may be used to control illumination sources in front and back illumination components 44, 46. In the examples of FIGS. 7-12, front and back illumination components 44, 46 each include eight separate illumination sources 60, 76. Each illumination source 60, 76 includes a red, green and blue illumination element, e.g., red, green and blue LEDs. Accordingly, FIG. 13 illustrates an exemplary control circuit 90 equipped to simultaneously drive eight different LEDs on a selective basis. In this manner, control circuit 90 may selectively activate all red LEDs to illuminate biological growth plate 22 with red light. Similarly, control circuit 90 may selectively activate all green or blue LEDs for green and blue illumination, respectively. FIG. 13 depicts control circuit 90 as controlling eight LEDs simultaneously, and hence controlling either front illumination component 44 or back illumination component 46. However, the output circuitry controlled by processor 34 may essentially be duplicated to permit control of sixteen LEDs simultaneously, and therefore both front illumination component 44 and back illumination component 46.

As shown in FIG. 13, processor 34 generates digital output values to drive a set of LEDs. Digital-to-analog converters (DAC) 91A-91H convert the digital output values to an analog drive signals. Buffer amplifiers 92A-92H amplify the analog signals produced by DACs 91A-91H and apply the amplified analog drive signals to respective arrays of LEDs 94A-94H, 96A-96H, 98A-98H. DACs 91A-91H and amplifiers 92A-92H serve as programmable controllers to selectively control illumination durations and illumination intensities of LEDS 94A-94H, 96A-96H, 98A-98H. Processor 34 drives the controllers, i.e., DACs 91A-91H and amplifiers 92A-92H, according to requirements of different biological growth plates 22 to be processed by scanner 10.

Advantageously, processor 34 may access particular sets of digital output values to produce a desired output intensity for LEDs 94A-94H, 96A-96H, 98A-98H. For example, the digital output values can be determined upon factory or field calibration of scanner 10 in order to enhance the uniformity of the illumination provided by the various LEDs 94A-94H, 96A-96H, 98A-98H. Again, the red, green and blue LEDs may be characterized by different output intensities and responses, and associated reflector and optics hardware may present nonuniformities, making independent control by processor 34 desirable in some applications.

Also, the digital output values may be determined based on the requirements of different biological growth plates 22, i.e., to control the intensity and duration of illumination applied to the growth plates. Accordingly, processor 34 may selectively generate different output values for different durations, enable different sets of LEDs 94-94H, 96A-96H, 98A-98H, and selectively enable either front illumination, back illumination or both, based on the particular types of biological growth plates 22 presented to scanner 10.

The anodes of all LEDs 94A-94H, 96A-96H, 98A-98H are coupled to the respective outputs of drive amplifiers 92A-92H for simultaneous activation of selected LEDs. To permit selective activation of LEDs for particular illumination colors, the cathodes of LEDs 94A-94H (Red) are coupled in common to a switch, e.g., to the collector of a bipolar junction transistor 100A with an emitter coupled to a ground potential. Similarly, the cathodes of LEDs 96A-96H (Green) are coupled in common to the collector of a bipolar junction transistor 100B, and the cathodes of LEDs 98A-98H (Blue) are coupled in common to the collector of a bipolar junction transistor 100C.

Processor 34 drives the base of each bipolar transistor 100A-100C with a RED ENABLE, GREEN ENABLE or BLUE ENABLE signal. In operation, to expose biological growth plate to red illumination, processor 34 selects digital values for the red LEDs 94A-94H, and applies the digital values to DACs 91A-91H, which produce analog drive signals for amplification by buffer amplifiers 92A-92H. In synchronization with application of the digital values for the red LEDs 94A-94H, processor 34 also activates the RED ENABLE line to bias transistor 100A "on," and thereby pull the anodes of red LEDs 94A-94H to ground.

Using the ENABLE lines, processor 34 can selectively activate red LEDs 94A-94H to expose biological growth plate 22 to red illumination. Simultaneously, processor 34 controls camera 42 to capture a red image of biological growth plate 22. To capture green and blue images, processor 34 generates appropriate digital drive values and activates the GREEN ENABLE and BLUE ENABLE lines, respectively. As an advantage, the ENABLE lines can be used to independently control the exposure durations of the illumination colors. For example, it may be desirable to expose biological growth plate 22 to different durations of red, green and blue illumination.

Figure 14:
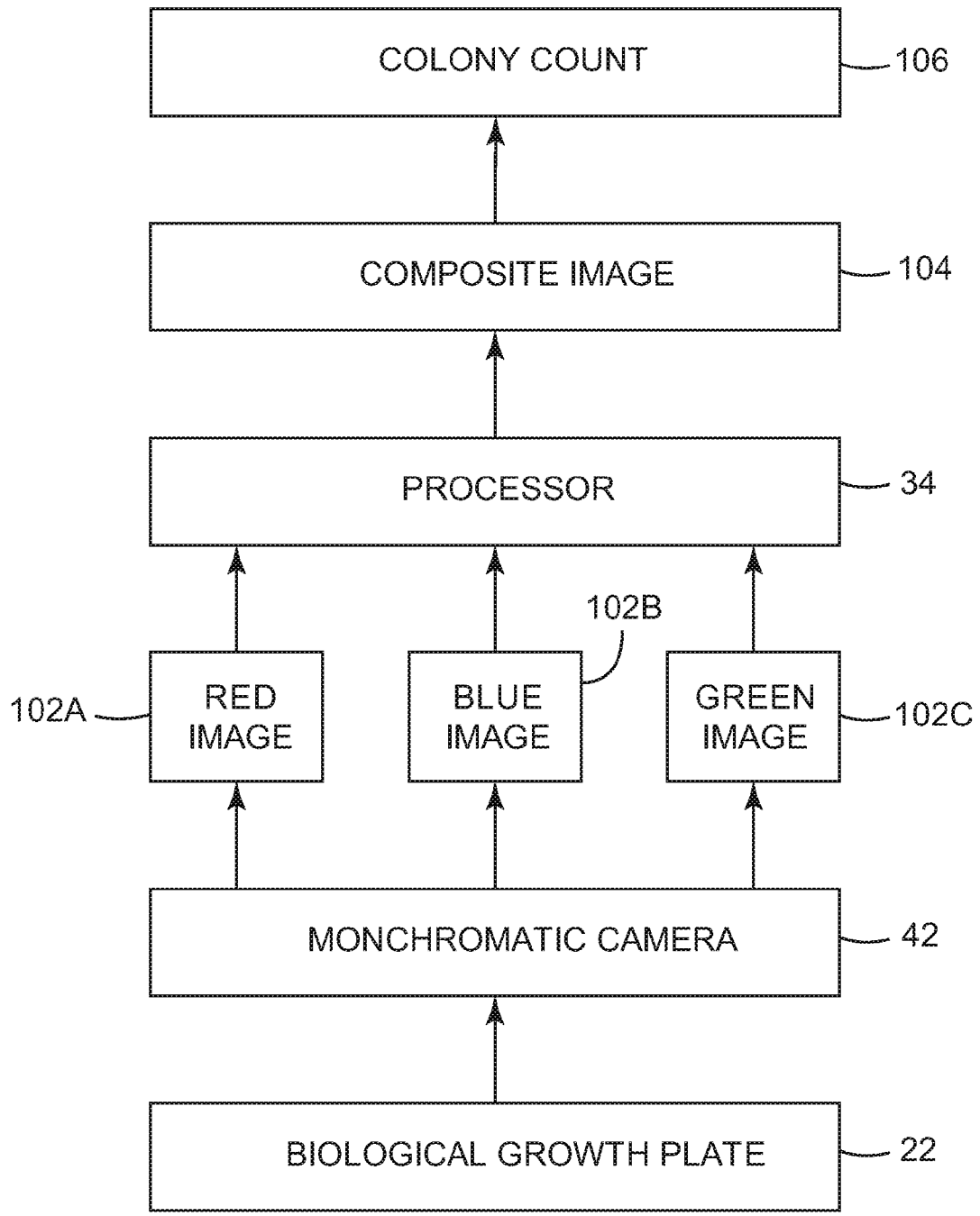
FIG. 14 is a functional block diagram illustrating the capture of multi-color images for preparation of a composite image to produce a plate count.

FIG. 14 is a functional block diagram illustrating the capture of multi-color images for preparation of a composite image to produce a plate count. As shown in FIG. 14, monochromatic camera 42 captures a red image 102A, green image 102B and blue image 102C from biological growth plate 22. Processor 34 then processes the red, green and blue images 102 to produce a composite image 104. In addition, processor 34 processes the composite image to produce an analytical result such as a colony count 106. Once the composite image has been prepared, combining the red, green and blue images, processor 34 may apply conventional image analysis techniques to produce the colony count.

Figure 15:
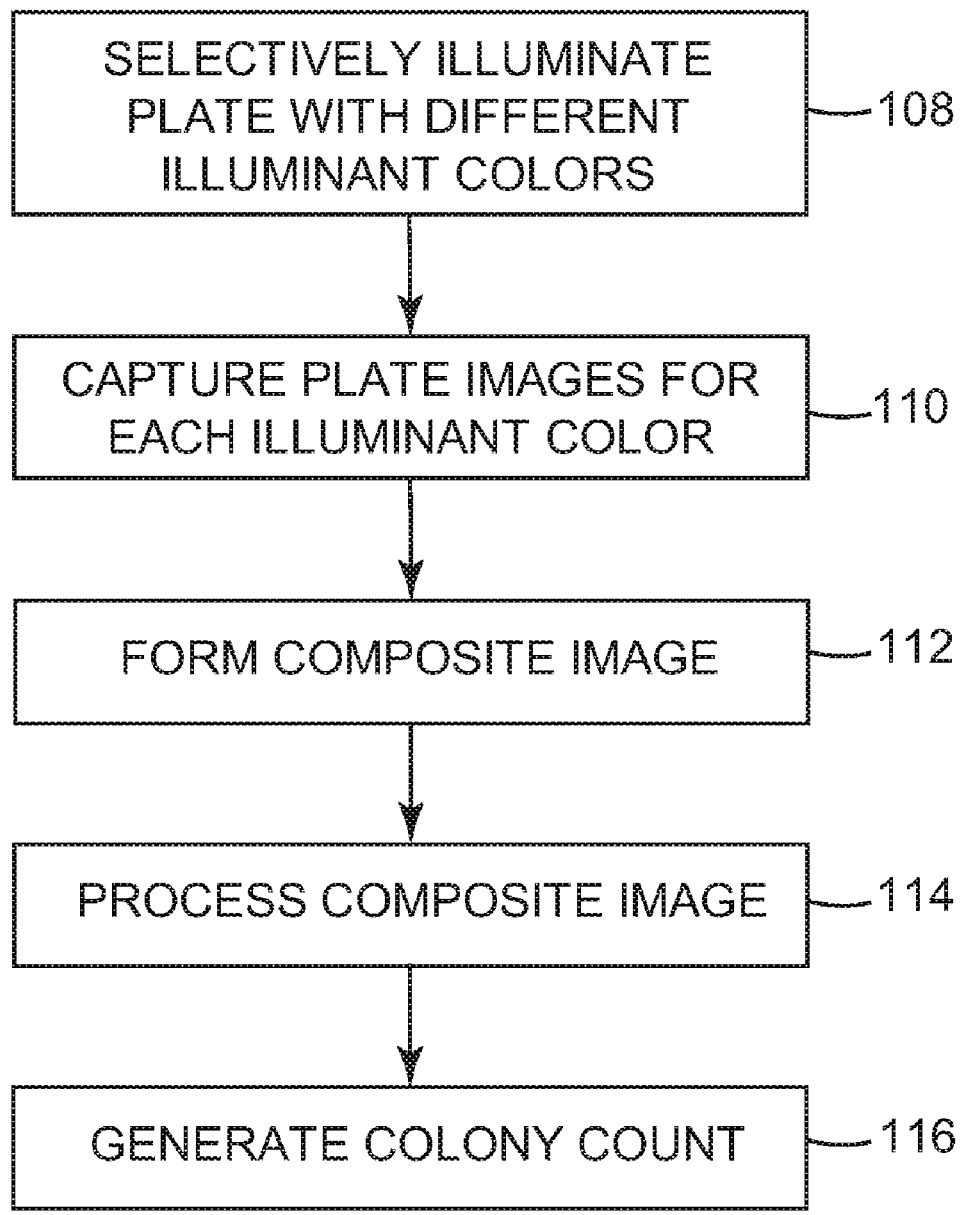
FIG. 15 is a flow diagram illustrating a technique for the capture of multi-color images for preparation of a composite image to produce a plate count.

FIG. 15 is a flow diagram illustrating a technique for the capture of multi-color images for preparation of a composite image to produce a plate count. As shown in FIG. 15, the technique may involve selective illuminating of a biological growth plate 22 with different illuminant colors (108), and capturing plate images during exposure to each of the illumination colors (110). The technique further involves forming a composite image (112) based on the separately captured images for each illumination color, and processing the composite image (114) to produce an analytical result such as a colony count (116). The colony count may be displayed to the user and logged to a date file. As mentioned above, techniques for capture of some images may involve illumination with one, two or more illumination colors, as well as front side illumination, back side illumination or both, depending on the requirements of the particular biological growth plate 22 to be processed by scanner 10.

Figure 16:
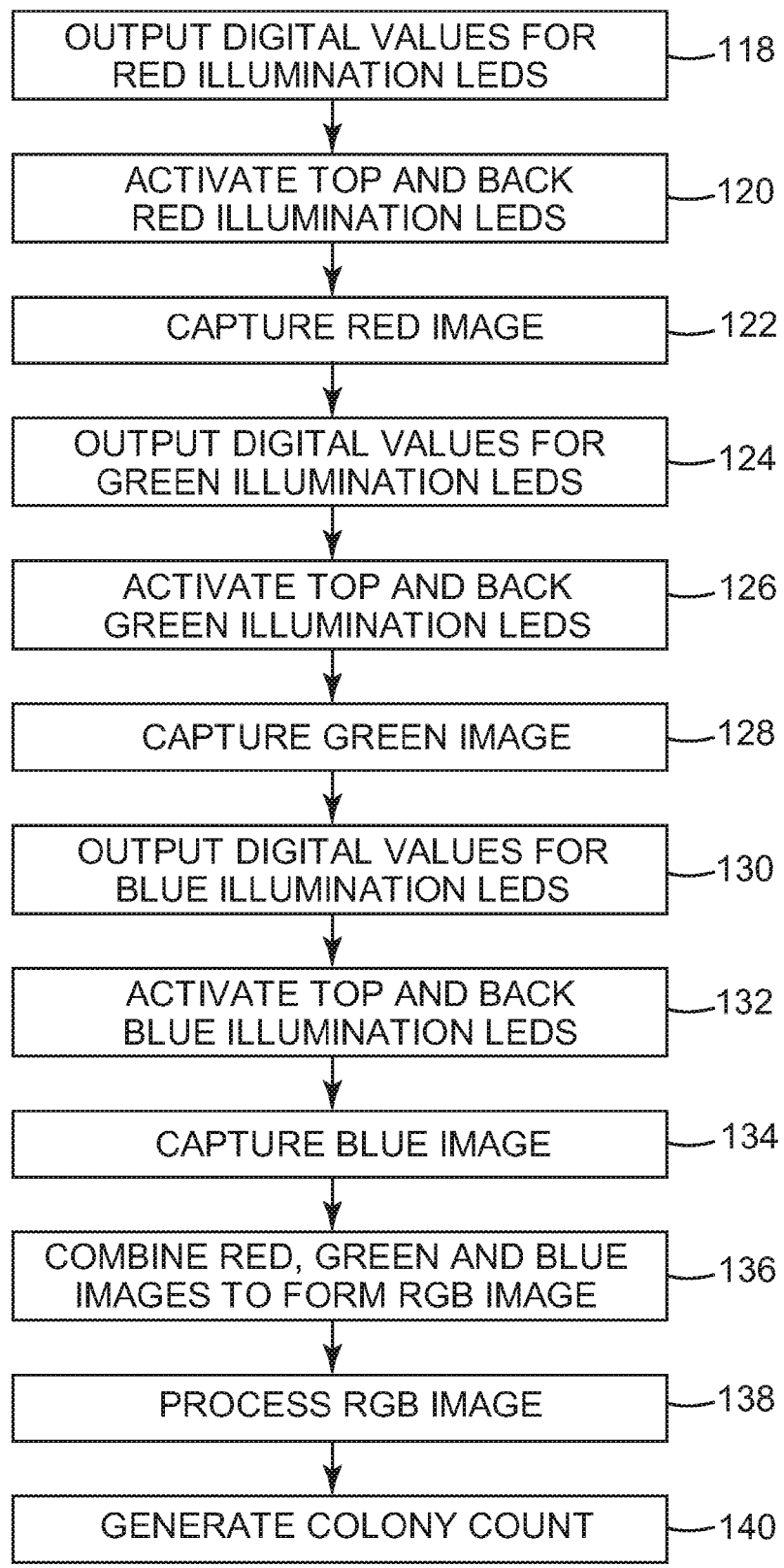
FIG. 16 is a flow diagram illustrating the technique of FIG. 15 in greater detail.

FIG. 16 is a flow diagram illustrating the technique of FIG. 15 in greater detail. As shown in FIG. 16, in operation, processor 34 first outputs digital values to drive the red illumination LEDs 94A-94H (FIG. 13) (118), and activates the front and back red illumination LEDs with the RED ENABLE line (120) to illuminate biological growth plate 22. Camera 42 then captures an image of biological growth plate 22 during illumination by the red LEDs 94A-94H (122).

Next, processor 34 outputs digital values to drive the green illumination LEDs 96A-96H (124), and activates the front and back green illumination LEDs with the GREEN ENABLE line (126) to illuminate biological growth plate 22. Camera 42 then captures an image of biological growth plate 22 during illumination by the green LEDs 96A-96H (128). Processor 34 then outputs digital value to drive the blue illumination LEDS 98A-98H (130), and activates the blue illumination LEDs with the BLUE ENABLE line (132).

After the blue image is captured by camera 42 (134), processor 34 combines the red, green and blue images to form a composite red-green-blue image (136). Processor 34 then processes the composite red-green-blue image (138) and/or individual components of the composite image to generate a colony count (140). Again, in some embodiments, processor 34 may process the individual red-green-blue images prior to combining the red, green and blue images to form a composite image. Again, the red-green-blue order of illumination and capture is described herein for purposes of example. Accordingly, biological growth plate 22 may be illuminated and scanned in a different order.

In operation, processor 34 executes instructions that may be stored on a computer-readable medium to carry out the processes described herein. The computer-readable medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like.

Various modifications may be made without departing from the spirit and scope of the invention. For example, it is conceivable that some of the features and principles described herein may be applied to line scanners as well as area scanners. These and other embodiments are within the scope of the following claims.

The invention claimed is:

1. A device for scanning biological growth plates that carry biological agents, the device comprising:
   a multi-color illumination system including light emitting diodes that selectively illuminates a biological growth plate with different illumination colors;
   a monochromatic camera oriented to capture an image of the biological growth plate; and
   a processor that controls the camera to capture two or more monochromatic images of the biological growth plate during illumination, wherein the processor combines the two or more monochromatic images to form a composite image of the biological growth plate and processes the composite image to generate a colony count associated with the biological growth plate, wherein the colony count is indicative of a counted number of colonies of the biological agents in the composite image,
   wherein the processor independently controls the light emitting diodes for different illumination colors so as to compensate for nonuniformities to achieve a degree of uniformity in the two or more monochromatic images;
   wherein the device quantifies an amount of bacterial colonies per unit area on the biological growth plate, and compares the amount to a threshold colony count to determine whether a sample on the biological growth plate is acceptable.

2. The device of claim 1, wherein the nonuniformities are due to different responses of the monochromatic camera to the different illumination colors.

3. The device of claim 1, wherein the nonuniformities are due to different brightness characteristics associated with the light emitting diodes and optical components of the multi-color illumination system.

4. The device of claim 1, wherein the multi-color illumination system includes a first illumination component that illuminates a first side of the biological growth plate and a second illumination component that illuminates a second side of the biological growth plate.

5. A method for scanning biological growth plates that carry biological agents, the method comprising:
   selectively illuminating a biological growth plate with light emitting diodes of different illumination colors;
   capturing two or more images of the biological growth plate using a monochromatic camera during illumination with each of the different illumination colors;

combining the two or more images captured by the monochromatic camera to form a composite image of the biological growth plate;

generating a colony count associated with the biological growth plate based on the composite image, wherein the colony count is indicative of a counted number of colonies of the biological agents in the composite image, quantifying an amount of bacterial colonies per unit area on the biological growth plate; and comparing the amount to a threshold to determine whether a sample on the biological growth plate is acceptable;

wherein selectively illuminating includes independently controlling the light emitting diodes for different illumination colors so as to compensate for nonuniformities to achieve a degree of uniformity in the two or more monochromatic images.

6. The method of claim 5, wherein the nonuniformities are due to different responses of the monochromatic camera to the different illumination colors.

7. The method of claim 5, wherein the nonuniformities are due to different brightness characteristics associated with the light emitting diodes and optical components of the multi-color illumination system.

8. A device for scanning biological growth plates that carry biological agents, the device comprising:

a multi-color illumination system including light emitting diodes that selectively illuminates a biological growth plate with different illumination colors;

a monochromatic camera oriented to capture an image of the biological growth plate; and a processor that controls the camera to capture two or more monochromatic images of the biological growth plate during illumination, wherein the processor combines the two or more monochromatic images to form a composite image of the biological growth plate and processes the composite image to generate a colony count associated with the biological growth plate, wherein the colony count is indicative of a counted number of colonies of the biological agents in the composite image, wherein the biological agents include an agent selected from a group consisting of aerobic bacteria, *E. coli*, coliform, enterobacteriaceae, yeast, mold, *Staphylococcus aureus, Listeria*, and *Campylobacter*, wherein the biological growth plates include plate type indicators and the device determines plate types based on the plate type indicators, wherein the processor selectively defines intensities and durations of illumination by the multi-color illumination system based on the plate types;

wherein the device quantifies an amount of bacterial colonies per unit area on the biological growth plate, and compares the amount to a threshold to determine whether a sample on the biological growth plate is acceptable.

9. The device of claim 8, wherein the processor independently controls the light emitting diodes for different illumination colors so as to compensate for nonuniformities to achieve a degree of uniformity in the two or more monochromatic images.

10. The device of claim 9, wherein the nonuniformities are due to different responses of the monochromatic camera to the different illumination colors.

11. The device of claim 9, wherein the nonuniformities are due to different brightness characteristics associated with the light emitting diodes and optical components of the multi-color illumination system.

12. The device of claim 8, wherein the multi-color illumination system includes a first illumination component that illuminates a first side of the biological growth plate and a second illumination component that illuminates a second side of the biological growth plate.

13. A method for scanning biological growth plates that carry biological agents, the method comprising:

selectively illuminating a biological growth plate with light emitting diodes of different illumination colors;

capturing two or more images of the biological growth plate using a monochromatic camera during illumination with each of the different illumination colors;

combining the two or more images captured by the monochromatic camera to form a composite image of the biological growth plate;

generating a colony count associated with the biological growth plate based on the composite image, wherein the colony count is indicative of a counted number of colonies of the biological agents in the composite image, wherein the biological growth plates include plate type indicators, and the method further comprises:

determining plate types based on the plate type indicators, selectively defining intensities and durations of illumination by the multi-color illumination system based on the plate types;

quantifying an amount of bacterial colonies per unit area on the biological growth plate; and comparing the amount to a threshold to determine whether a sample on the biological growth plate is acceptable.

14. The method of claim 13, wherein selectively illuminating includes independently controlling the light emitting diodes for different illumination colors so as to compensate for nonuniformities to achieve a degree of uniformity in the two or more monochromatic images.

15. The method of claim 14, wherein the nonuniformities are due to different responses of the monochromatic camera to the different illumination colors.

16. The method of claim 14, wherein the nonuniformities are due to different brightness characteristics associated with the light emitting diodes and optical components of the multi-color illumination system.

* * * * *